US 8,353,820 B2

(12) United States Patent
Karasawa et al.

(10) Patent No.: US 8,353,820 B2
(45) Date of Patent: Jan. 15, 2013

(54) MEDICAL APPARATUS

(75) Inventors: Hitoshi Karasawa, Hachioji (JP); Sho Nakajima, Hachioji (JP); Daisuke Asada, Hachioji (JP); Nobuyoshi Yazawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 641 days.

(21) Appl. No.: 12/536,145

(22) Filed: Aug. 5, 2009

(65) Prior Publication Data

US 2010/0036199 A1 Feb. 11, 2010

(30) Foreign Application Priority Data

Aug. 5, 2008 (JP) ................................. 2008-202212

(51) Int. Cl.
*A61B 1/32* (2006.01)
(52) U.S. Cl. ........................................ 600/124; 600/174
(58) Field of Classification Search ................ 600/124
See application file for complete search history.

(56) References Cited

U.S. PATENT DOCUMENTS

| 5,381,784 A * | 1/1995 | Adair | 600/166 |
| 6,067,116 A * | 5/2000 | Yamano et al. | 348/372 |
| 6,419,626 B1 * | 7/2002 | Yoon | 600/109 |
| 2006/0155168 A1 * | 7/2006 | Pease | 600/131 |
| 2010/0036199 A1 * | 2/2010 | Karasawa et al. | 600/109 |

FOREIGN PATENT DOCUMENTS

| JP | 5-68666 A | 3/1993 |
| JP | 7-143368 A | 6/1995 |
| JP | 10-243266 A | 9/1998 |
| JP | 2005-073884 | 3/2005 |
| JP | 2007-014634 | 1/2007 |
| JP | 2008-500110 | 1/2008 |

OTHER PUBLICATIONS

Abstract of International Publication No. WO 2005/115237 A2, dated Dec. 8, 2005.

* cited by examiner

*Primary Examiner* — Clayton E Laballe
*Assistant Examiner* — Bret Adams
(74) *Attorney, Agent, or Firm* — Scully Scott Murphy & Presser, PC

(57) ABSTRACT

A medical apparatus according to the present invention includes: an image pickup section including an observation window, the image pickup section being led into a body; a holding section that holds the image pickup section inside the body; a covering section that is connected to the holding section and covers the observation window to set the image pickup section in a non-photographable state; and a field-of-view control section that variably controls the covering of the observation window by the covering section and sets the image pickup section in a photographable state to allow the image pickup section to photograph a subject inside the body.

14 Claims, 32 Drawing Sheets

MEDICAL APPARATUS

This application claims benefit of Japanese Application No. 2008-202212 filed in Japan on Aug. 5, 2008, the contents of which are incorporated by this reference.

BACKGROUND OF THE INVENTION

1. Field of the Invention

The present invention relates to a medical apparatus including a medical instrument for photographing the inside of a body.

2. Description of the Related Art

As is well known, an endoscope as a medical instrument includes an image pickup apparatus. The endoscope is led into a body cavity of a patient and used for performing various inspections, various kinds of treatments, and the like for an affected area in the body using observation images photographed by the image pickup apparatus.

Examples of such an endoscope include an endoscope that is led into digestive organs such as the esophagus, the stomach, the large intestine, and the duodenum, which are luminal tracts in the body, from the anus or the mouth cavity and an endoscope that is led into the abdominal cavity penetrating through the body wall from the vicinity of the navel. In general, the endoscope has a long insertion portion. The insertion portion is inserted into the digestive tract or into the abdominal cavity.

In recent years, in order to reduce pain to a patient due to the insertion of the insertion portion, for example, capsule type medical devices disclosed in Japanese Patent Application Laid-Open Publication No. 2008-500110, Japanese Patent Application Laid-Open Publication No. 2005-73884, and Japanese Patent Application Laid-Open Publication No. 2007-14634 are proposed.

Japanese Patent Application Laid-Open Publication No. 2008-500110 discloses a delivery device that directly delivers a capsule device, which is a capsule type medical device, by holding the capsule device to a targeted position in the body cavity such as the stomach or the small intestine and discharging the capsule device.

Japanese Patent Application Laid-Open Publication No. 2005-73884 discloses a technique for a protective device for a radio intra-subject information acquiring device that surrounds a pill, which is a capsule type endoscope, using a protective cap, which is a protective device, and suppresses careless radio wave radiation related to communication with an external device.

Japanese Patent Application Laid-Open Publication No. 2007-14634 discloses a technique for a capsule placement medical device that places a capsule type endoscope in the body cavity and prevents the surface of a distal end portion cover housing of the capsule type endoscope with a dome-like hood section, which covers an entire observation field of view of the capsule type endoscope, to reduce the influence on observation as much as possible.

SUMMARY OF THE INVENTION

A medical apparatus according to the present invention includes: an image pickup section including an observation window, the image pickup section being led into a body; a holding section that holds the image pickup section inside the body; a covering section that is connected to the holding section and covers the observation window to set the image pickup section in a non-photographable state; and a field-of-view control section that variably controls the covering of the observation window by the covering section and sets the image pickup section in a photographable state to allow the image pickup section to photograph a subject inside the body. This makes it possible to prevent an observation window of an observation optical system and an illumination window of an illumination optical system from being soiled when the medical apparatus is led into the body cavity and the abdominal cavity, prevent a field of view during use from being deteriorated and irradiation of illumination light from being disturbed, and acquire a clear observation image.

The above and other objects, features and advantages of the invention will become more clearly understood from the following description referring to the accompanying drawings.

DETAILED DESCRIPTION OF THE PREFERRED EMBODIMENTS

Embodiments of the present invention are explained below with reference to the accompanying drawings. In the following explanation, for example, a medical apparatus for performing a laparoscopic surgical operation is illustrated.

First Embodiment

Figure 1:
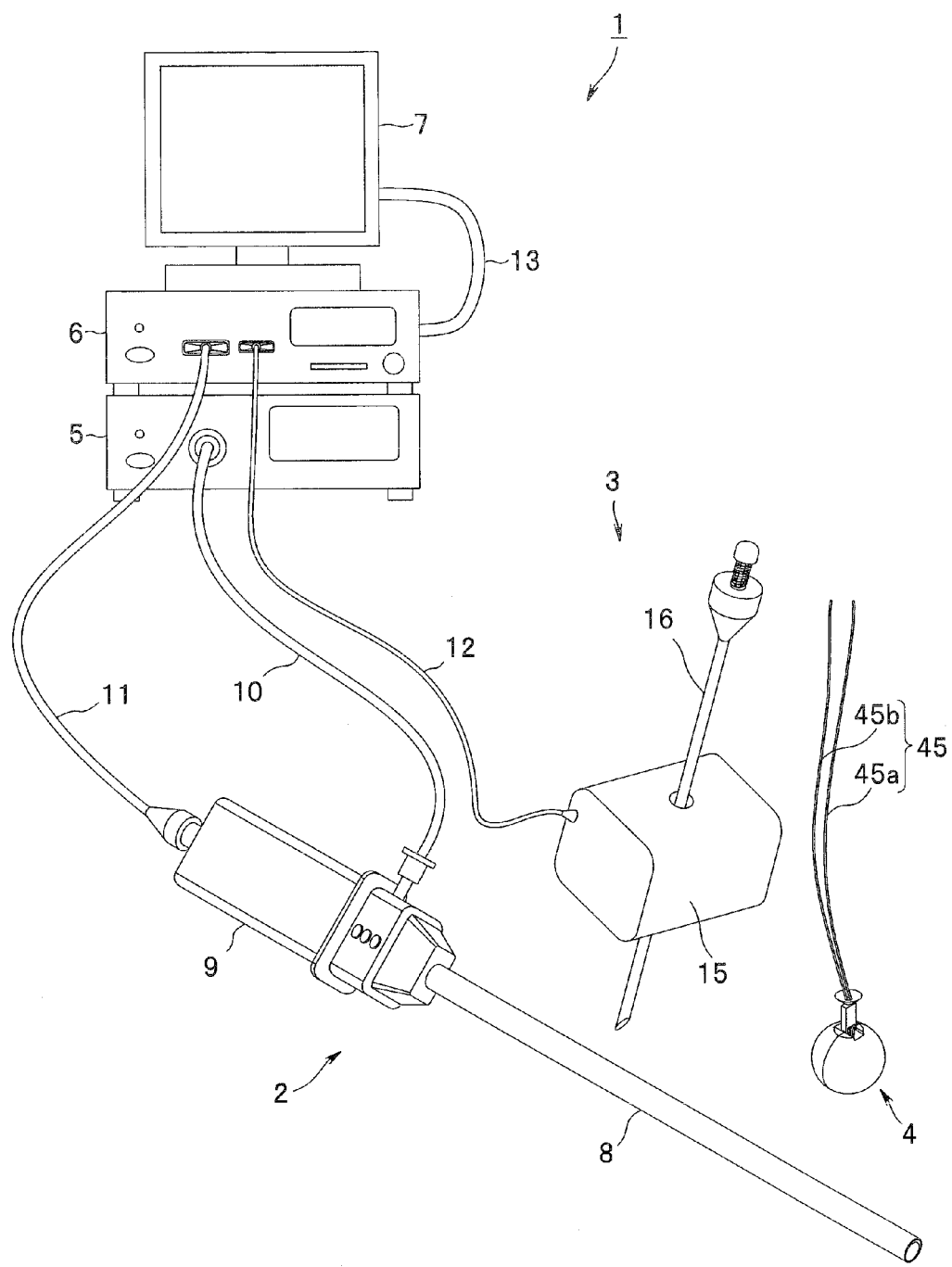
FIG. 1 is a diagram of a configuration of an endoscope system as a medical apparatus according to a first embodiment of the present invention.
Figure 2:
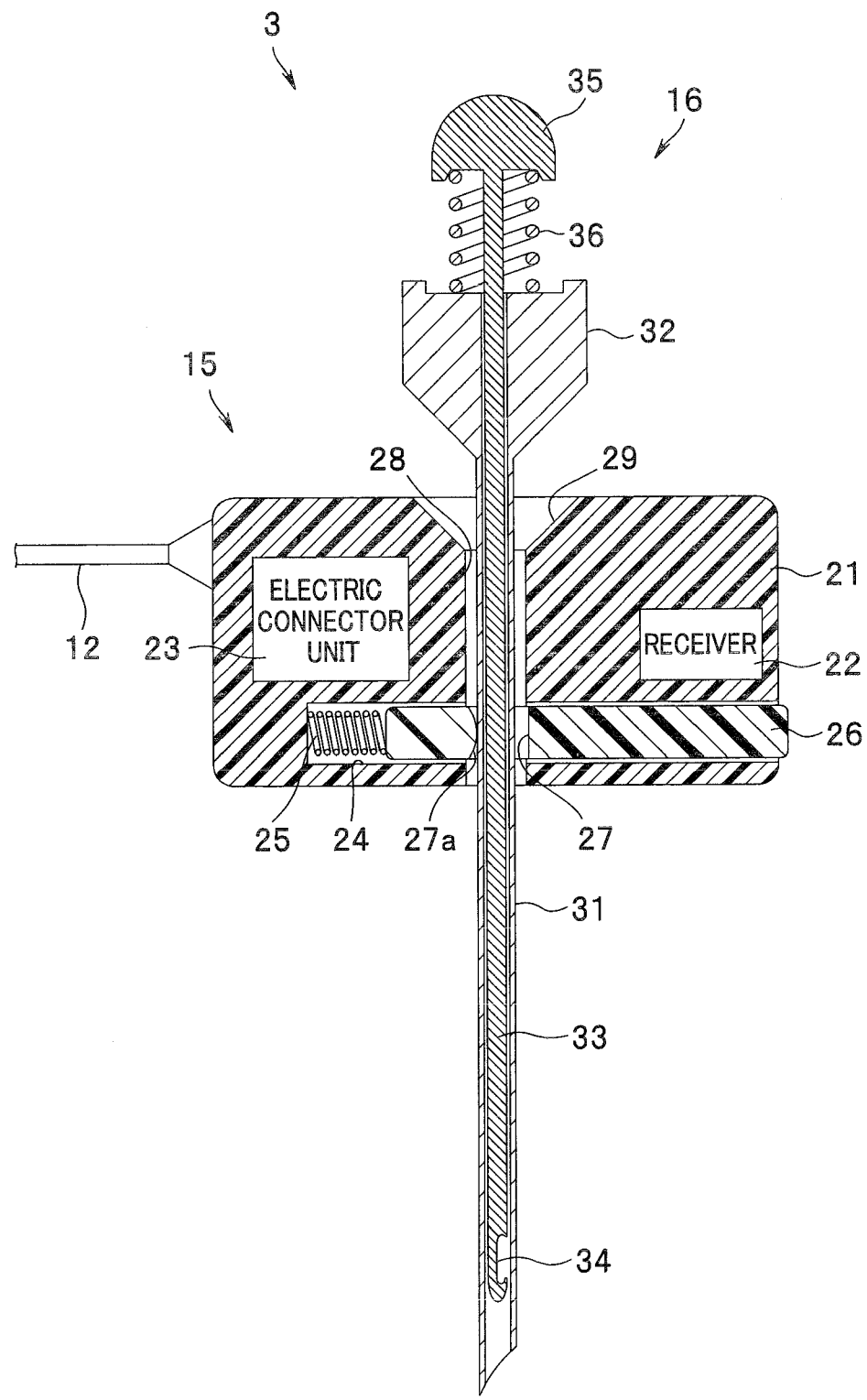
FIG. 2 is a sectional view of a configuration of an external device according to the first embodiment.
Figure 3:
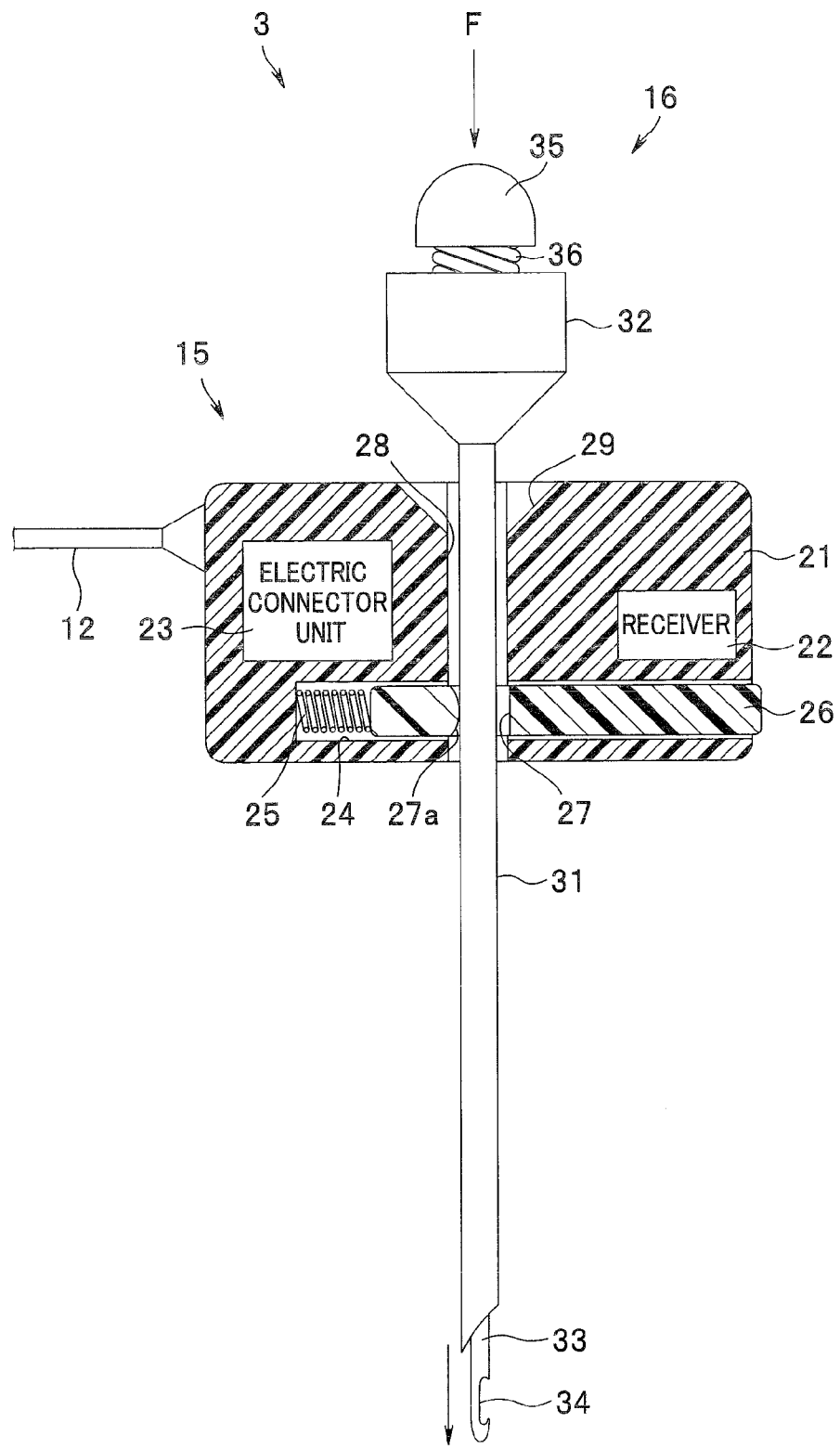
FIG. 3 is a sectional view of an action of a penetrating needle of the external device according to the first embodiment.
Figure 4:
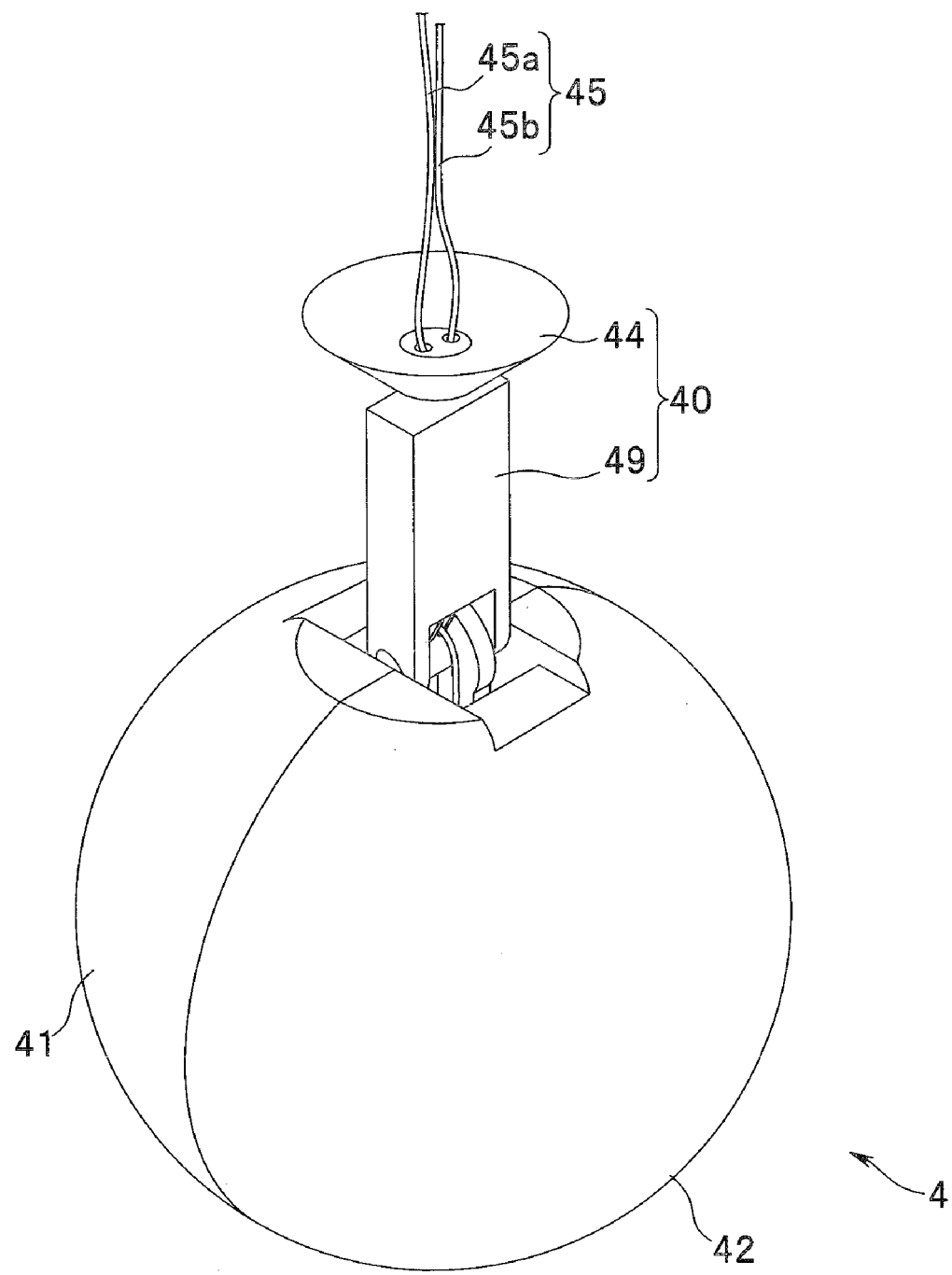
FIG. 4 is a perspective view of a configuration of an intra-abdominal cavity set camera according to the first embodiment.
Figure 5:
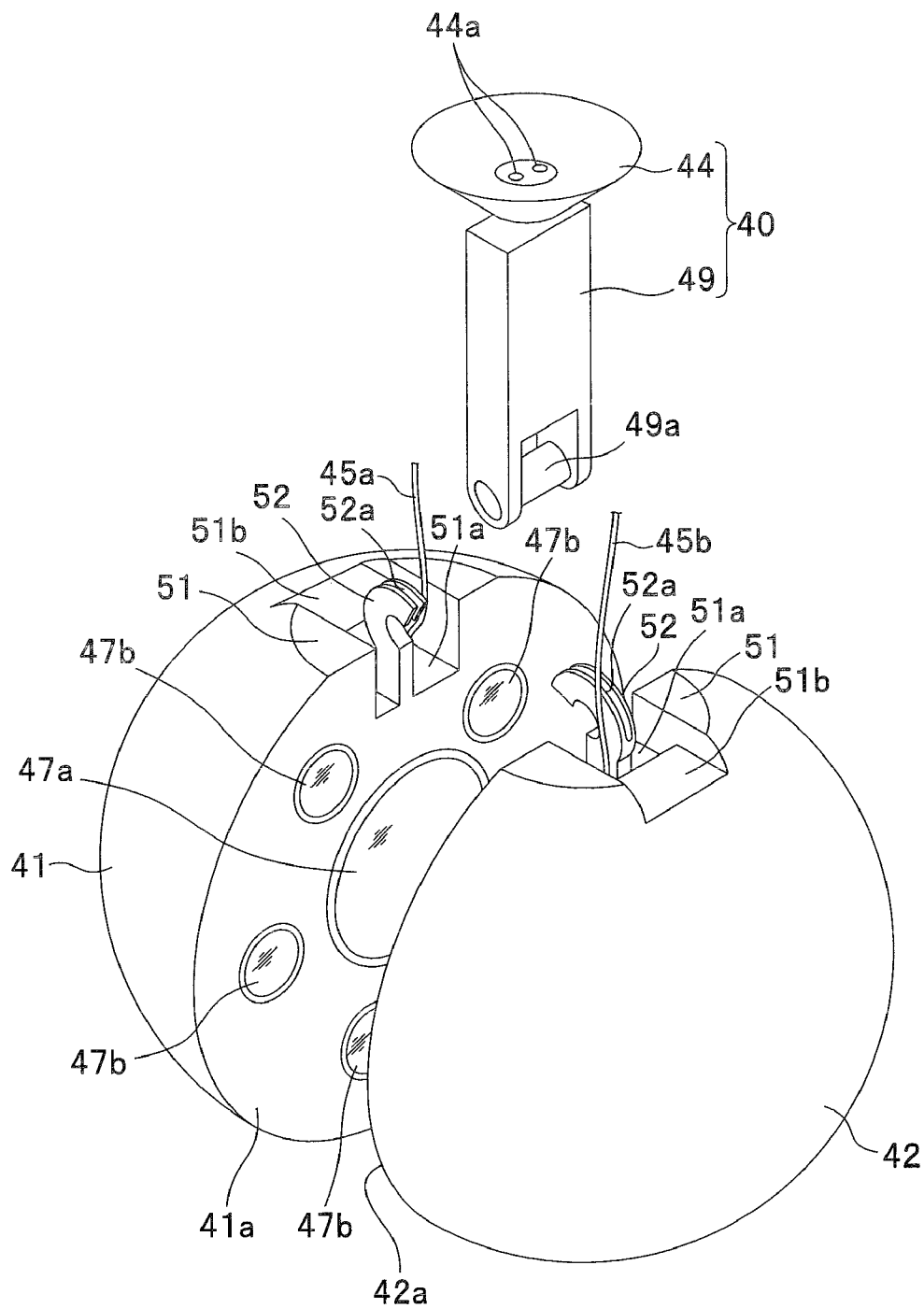
FIG. 5 is an exploded perspective view of the configuration of the intra-abdominal cavity set camera according to the first embodiment.
Figure 6:
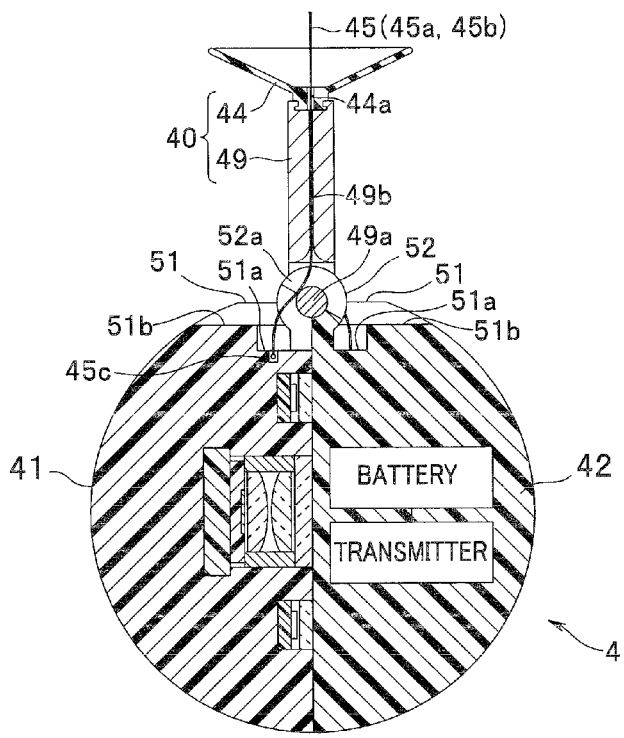
FIG. 6 is a sectional view of a state in which the intra-abdominal cavity set camera is closed in the first embodiment.
Figure 7:
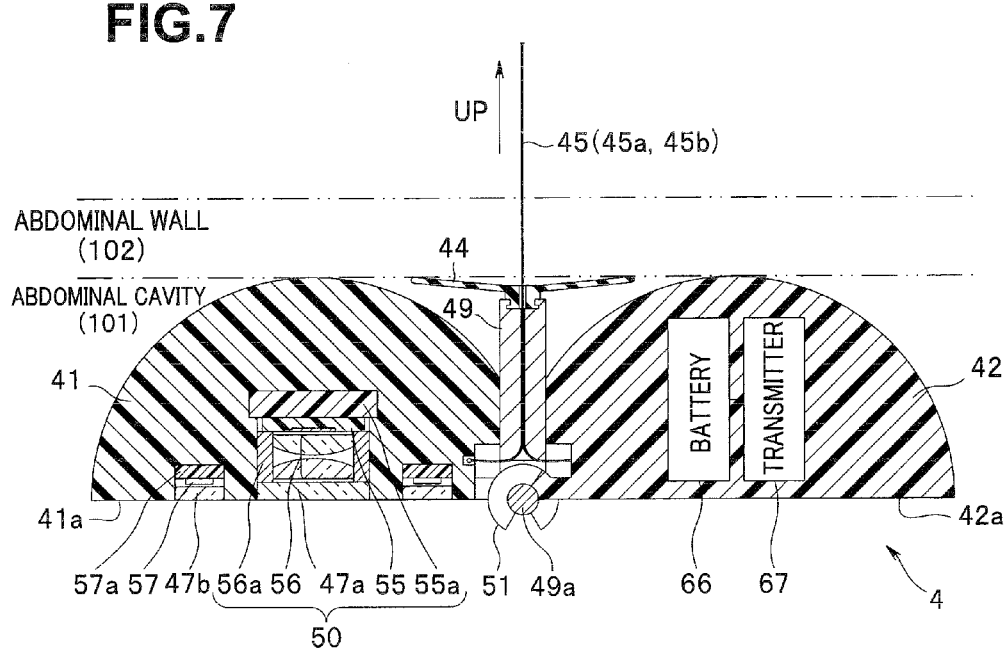
FIG. 7 is a sectional view of a state in which the intra-abdominal cavity set camera is fixed to the abdominal wall and opened in the first embodiment.
Figure 8:
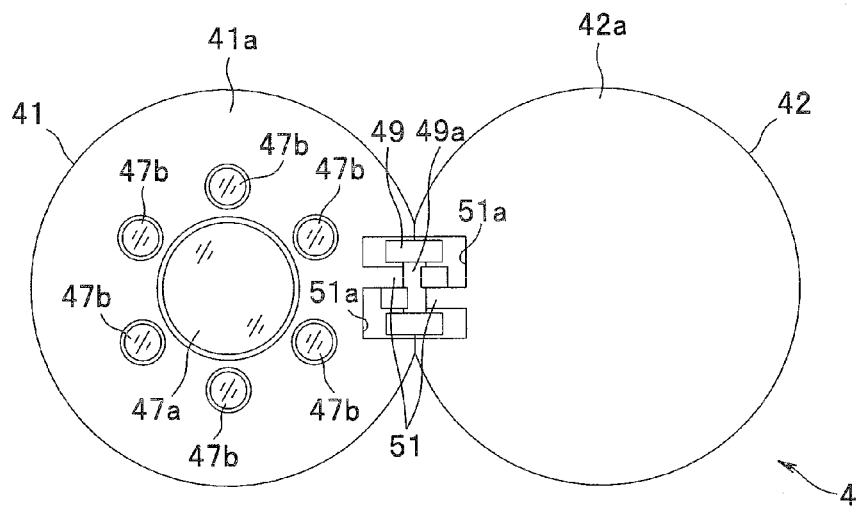
FIG. 8 is a plan view of a layout of an observation window and illumination windows of the intra-abdominal cavity set camera according to the first embodiment.
Figure 9:
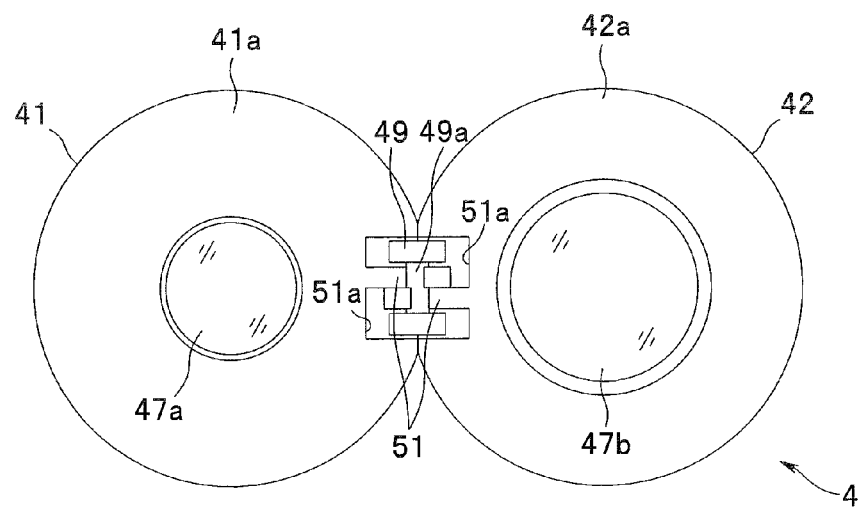
FIG. 9 is a plan view of a layout of an observation window and an illumination window of an intra-abdominal cavity set camera according to a first modification of the first embodiment.
Figure 10:
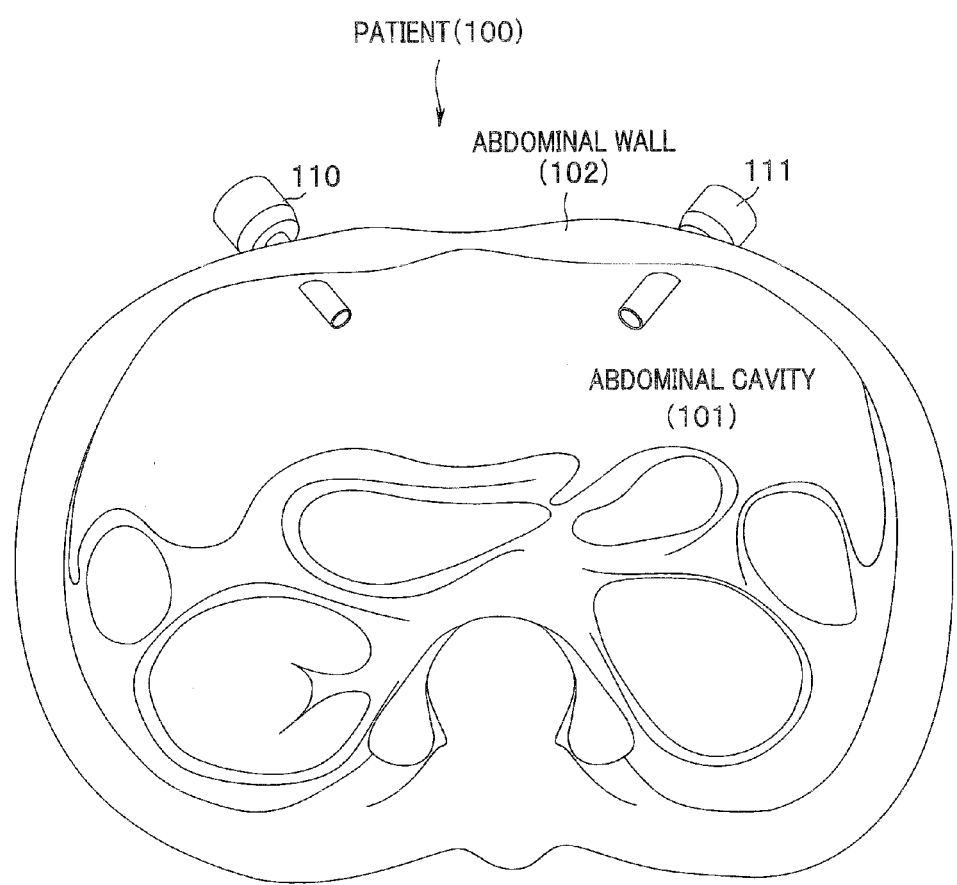
FIG. 10 is a diagram of a state in which trocars are penetrated into the abdominal wall of a patient in the first embodiment.
Figure 11:
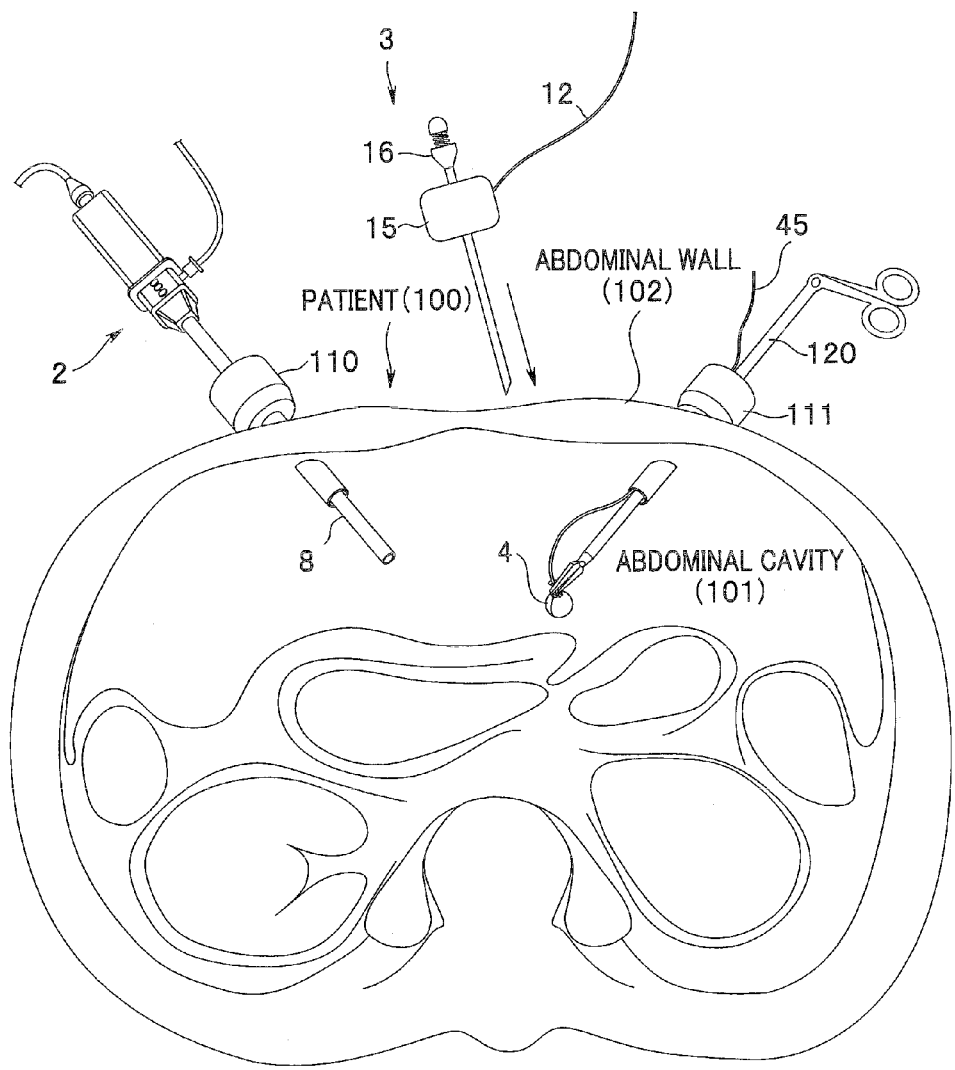
FIG. 11 is a diagram for explaining a procedure for leading the intra-abdominal cavity set camera into the abdominal cavity in the first embodiment.
Figure 12:
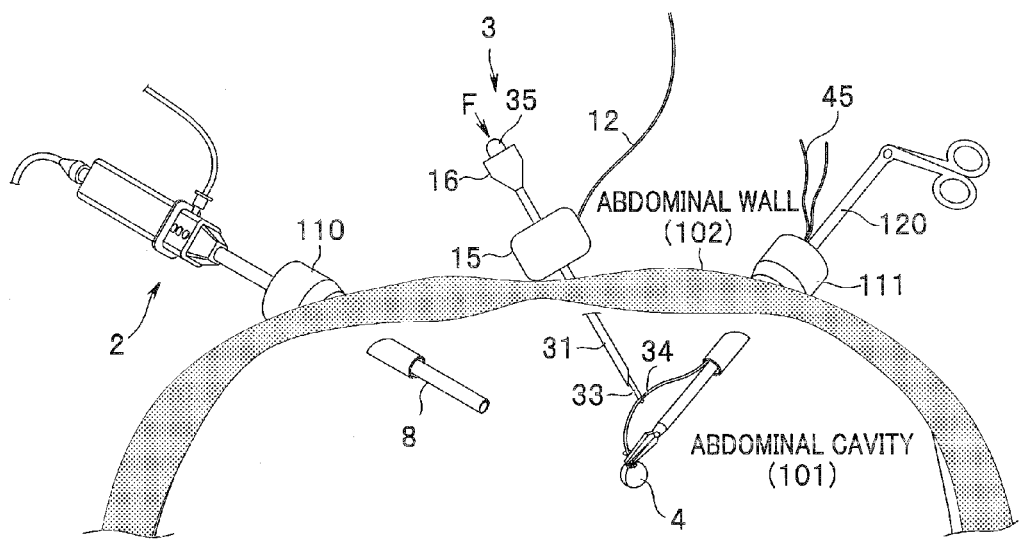
FIG. 12 is a diagram of a state in which a hook needle is penetrated into the abdominal wall and a wire bundle of the intra-abdominal cavity set camera is hooked and for explaining a procedure for leading the intra-abdominal cavity set camera into the abdominal cavity in the first embodiment.
Figure 13:
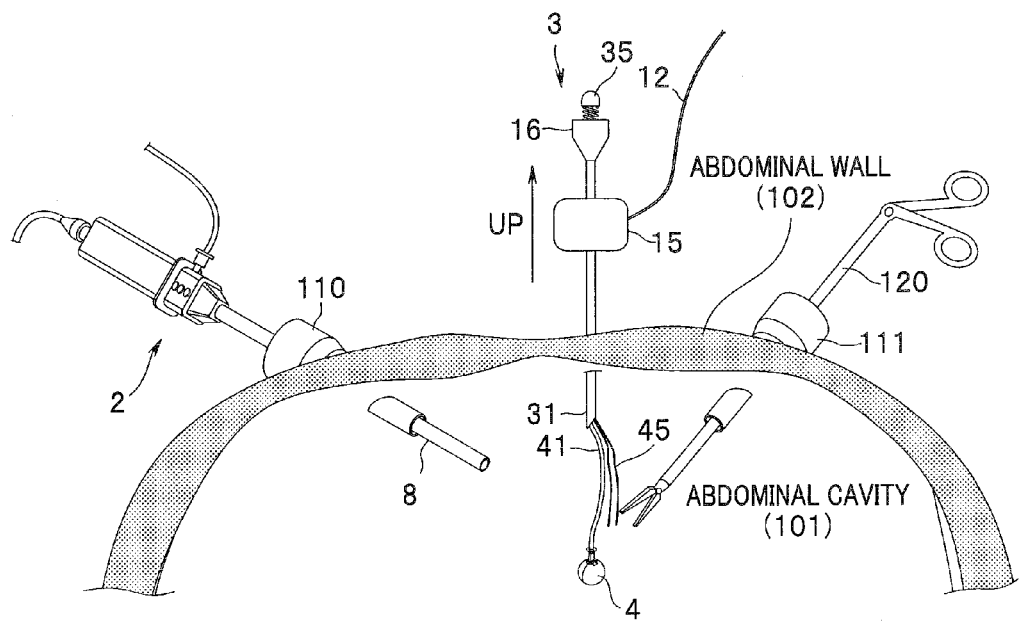
FIG. 13 is a diagram of a state in which the hook needle that hooks the wire bundle of the intra-abdominal cavity set camera is pulled up and for explaining a procedure for fixing the intra-abdominal cavity set camera to the abdominal wall in the first embodiment.
Figure 14:
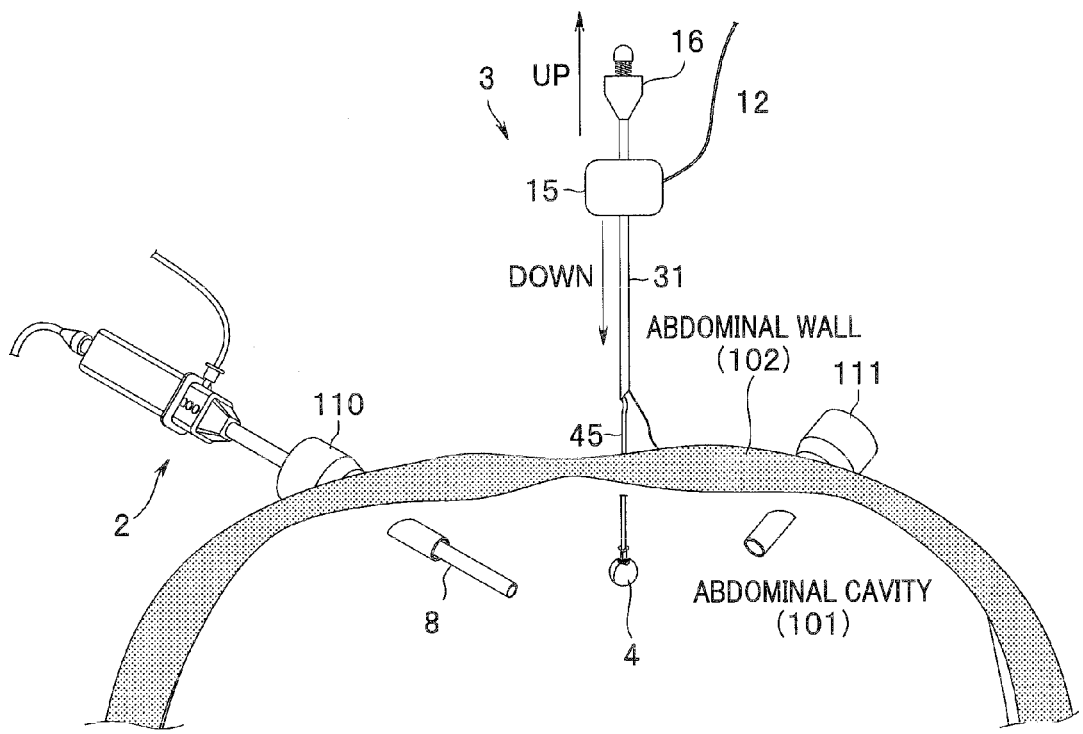
FIG. 14 is a diagram of a state in which the hook needle is pulled up and a fixing unit is lowered along the hook needle and for explaining a procedure for fixing the intra-abdominal cavity set camera to the abdominal wall in the first embodiment.
Figure 15:
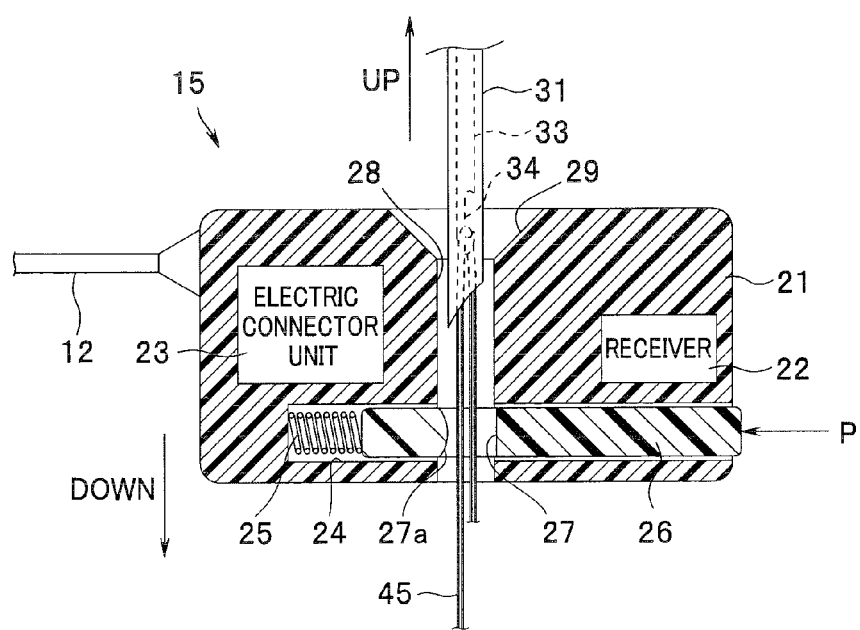
FIG. 15 is a sectional view for explaining an action of the external device according to the first embodiment.
Figure 16:
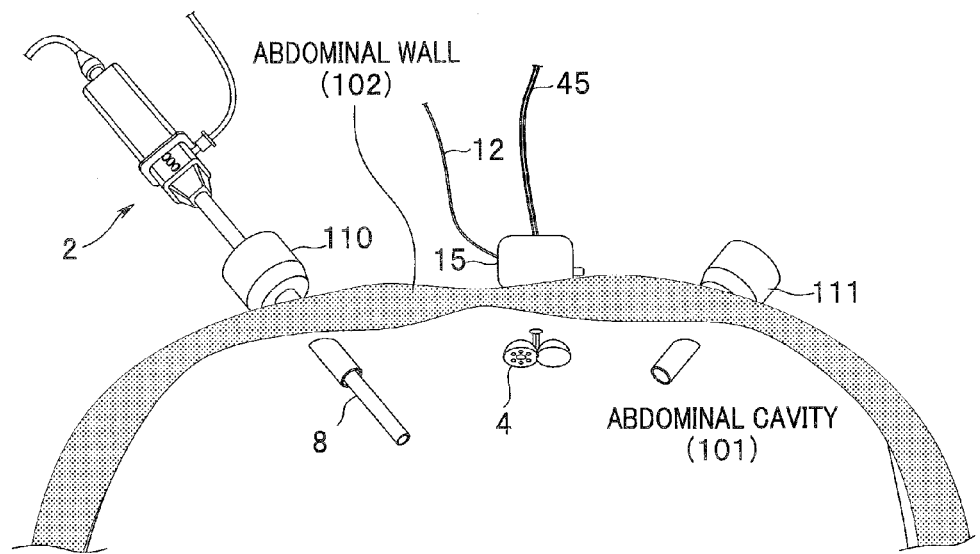
FIG. 16 is a diagram of a state in which the fixing unit is set on the abdomen and the intra-abdominal cavity set camera is fixed to the abdominal wall in the first embodiment.
Figure 17:
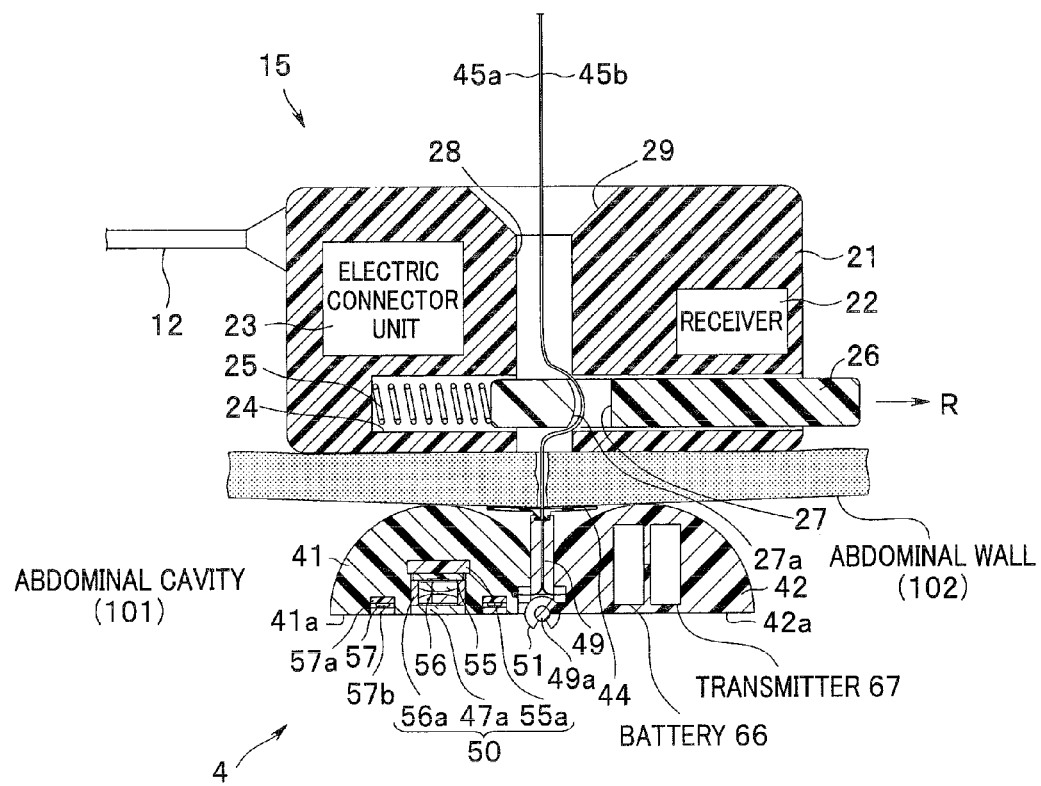
FIG. 17 is a sectional view of the fixing unit and the intra-abdominal set camera in the state shown in FIG. 16 in the first embodiment.
Figure 18:
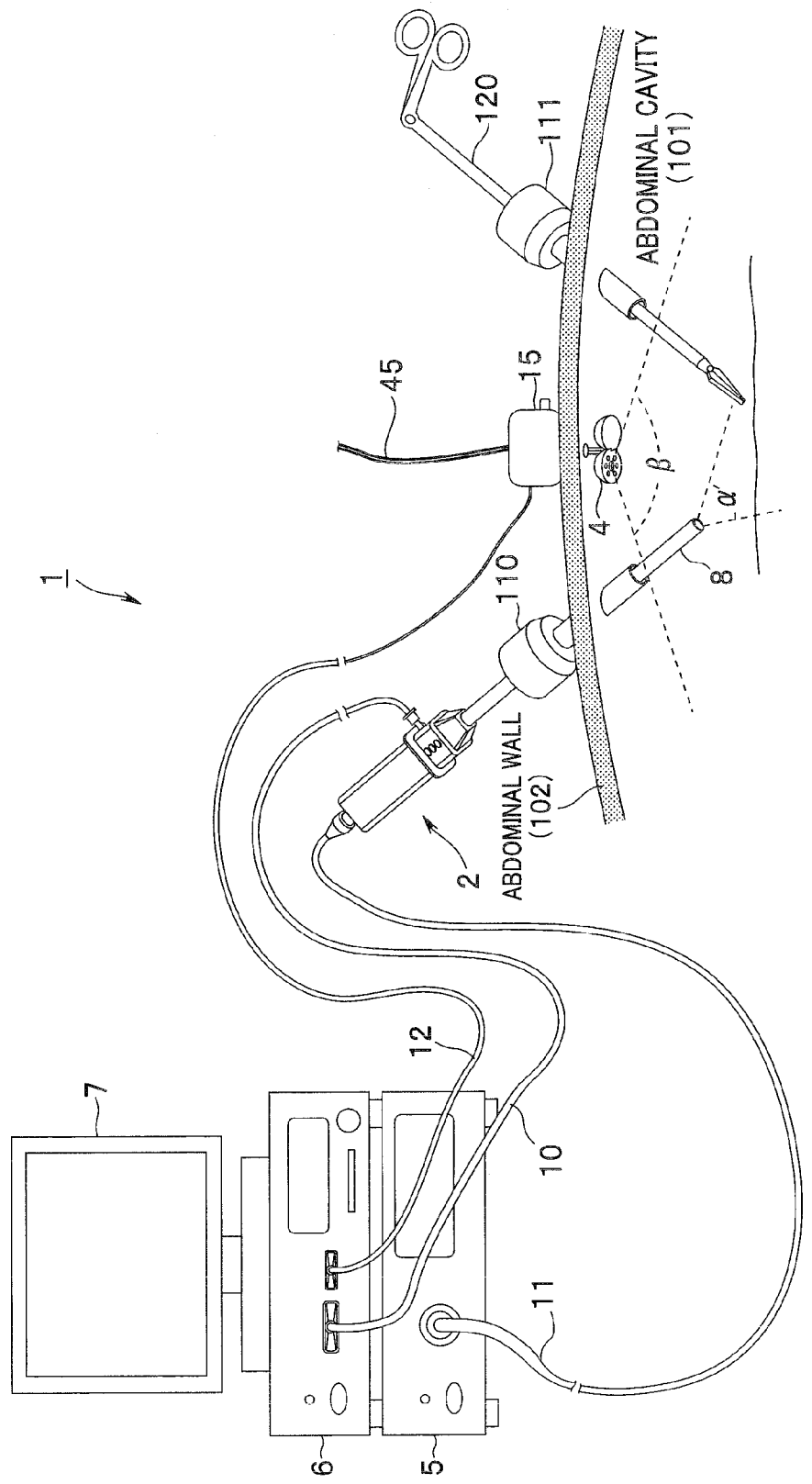
FIG. 18 is an overall diagram of the endoscope system in a state in which the intra-abdominal cavity set camera is fixed to the abdominal wall in the first embodiment.
Figure 19:
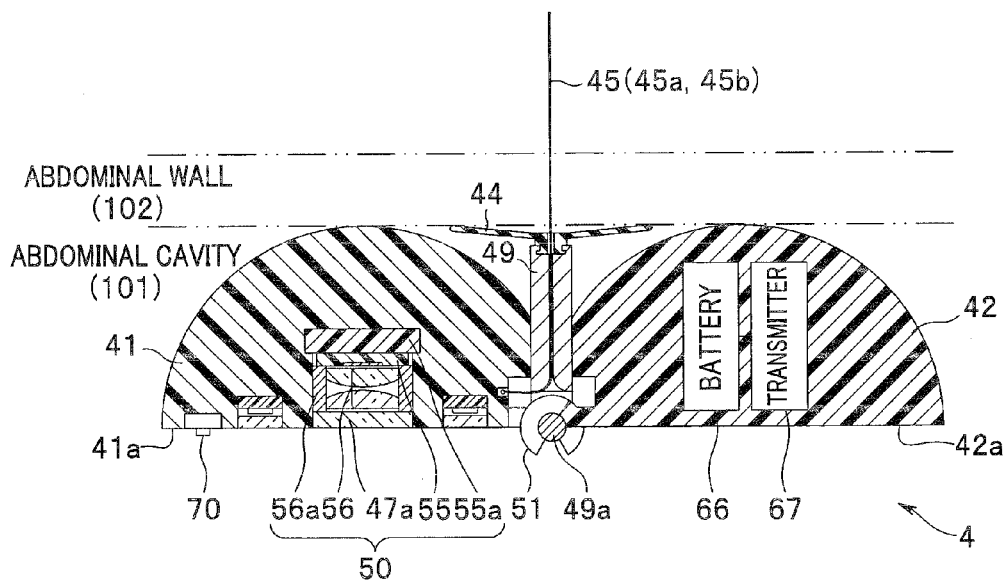
FIG. 19 is a sectional view of a configuration of an intra-abdominal cavity set camera according to a second modification of the first embodiment in which a switch for controlling ON and OFF of an electric function is provided.
Figure 20:
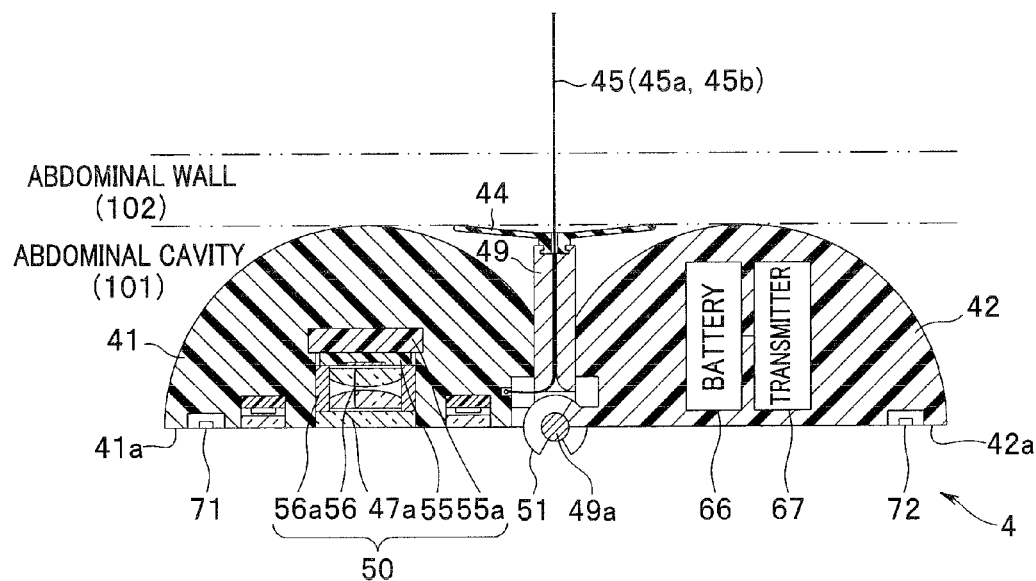
FIG. 20 is a sectional view of a configuration of the intra-abdominal cavity set camera shown in FIG. 19 according to the second modification in which the switch for controlling ON and OFF of the electric function is changed to an optical sensor.
Figure 21:
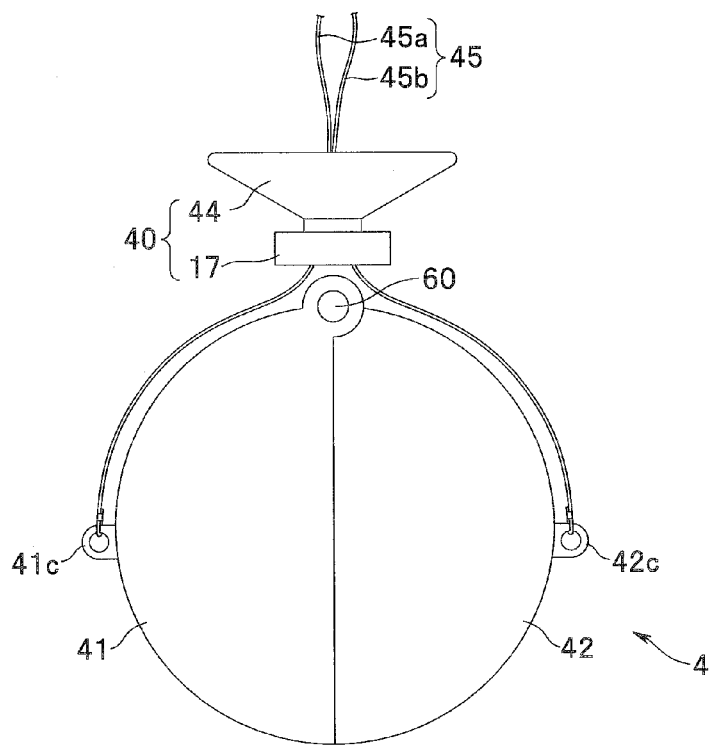
FIG. 21 is a side view of an intra-abdominal cavity set camera according to a third modification of the first embodiment in a closed state.
Figure 22:
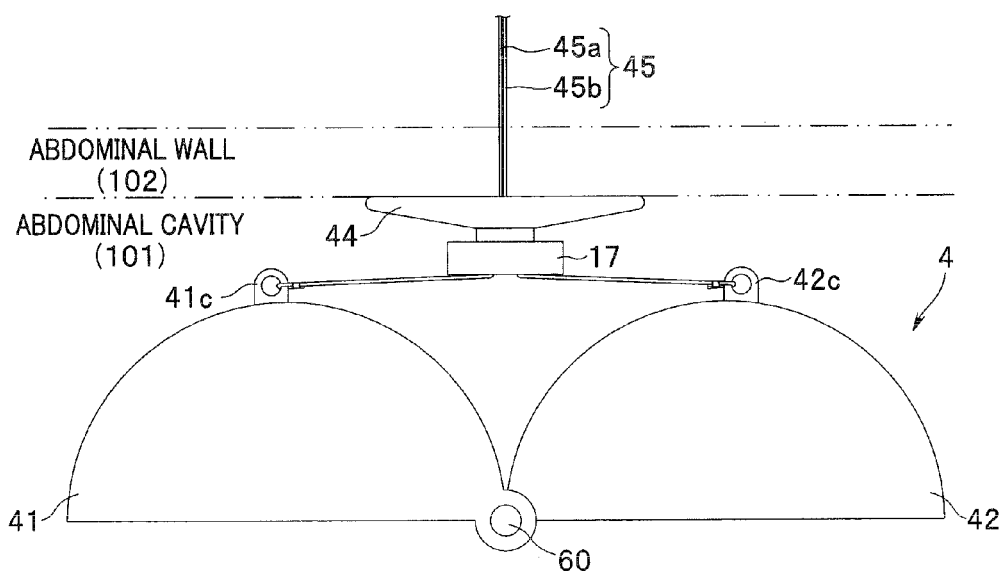
FIG. 22 is a diagram of a state in which the intra-abdominal cavity set camera shown in FIG. 21 according to the third modification is fixed to the abdominal wall.
Figure 23:
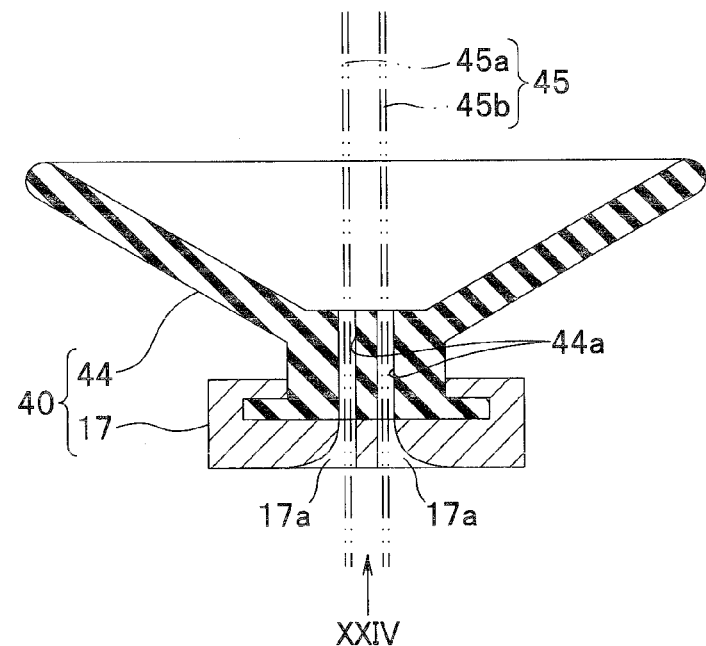
FIG. 23 is a sectional view of an abdominal wall fixing unit of the intra-abdominal cavity set camera shown in FIG. 22 according to the third modification.
Figure 24:
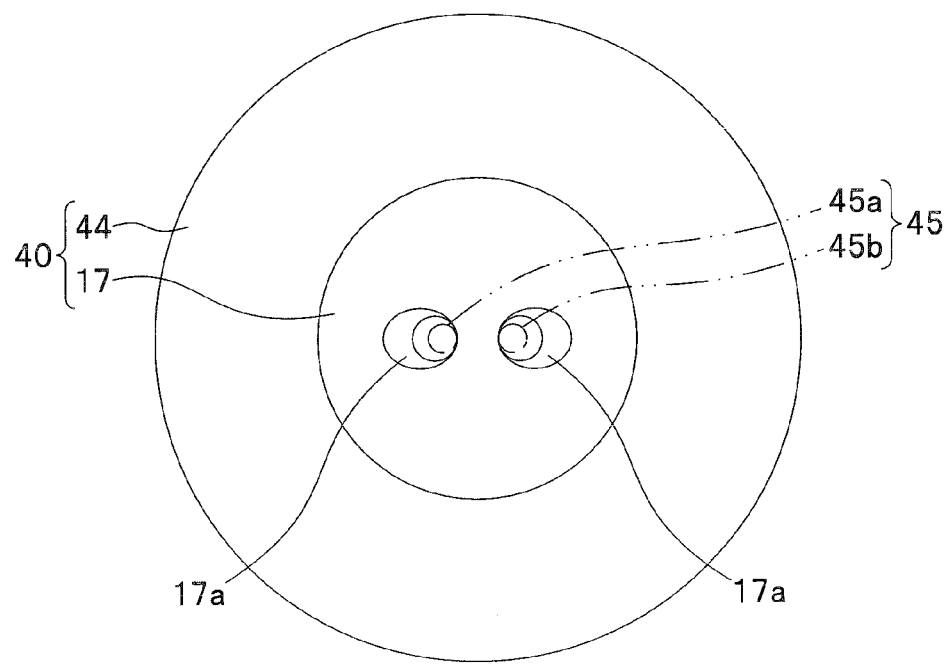
FIG. 24 is a plan view of the intra-abdominal cavity set camera shown in FIG. 23 according to the third modification viewed from an arrow XXIV direction.
Figure 25:
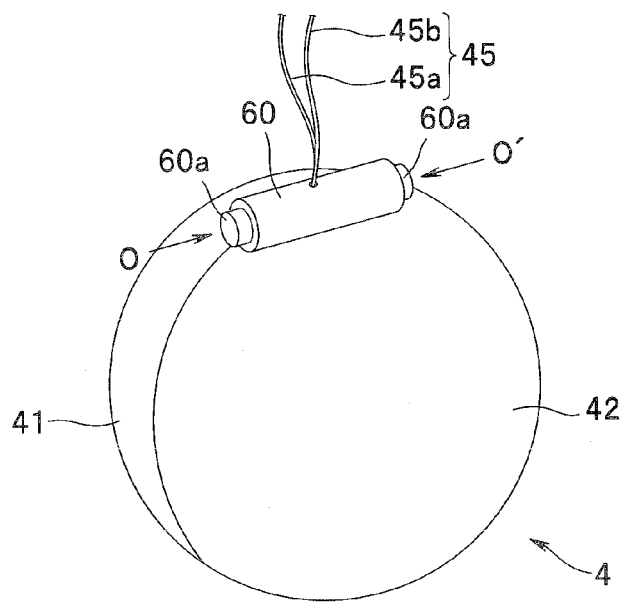
FIG. 25 is a perspective view of a configuration of an intra-abdominal cavity set camera according to a fourth modification of the first embodiment in which an opening button is provided in a hinge mechanism.
Figure 26:
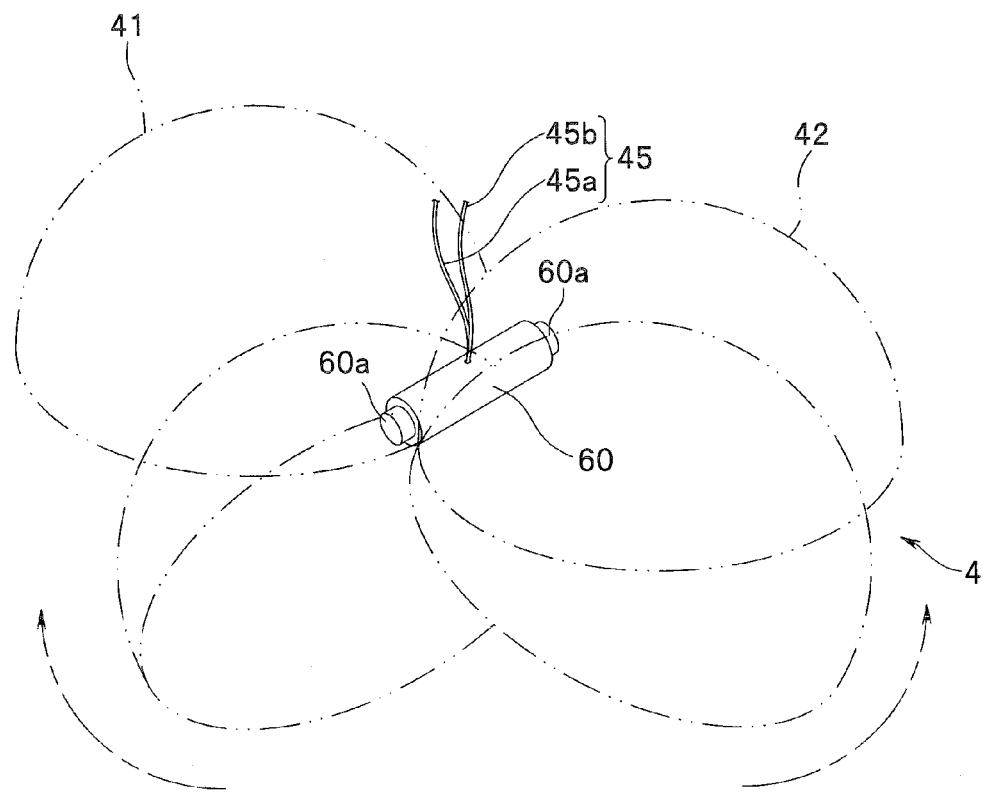
FIG. 26 is a perspective view of an opening action of the intra-abdominal cavity set camera shown in FIG. 25 according to the fourth modification.
Figure 27:
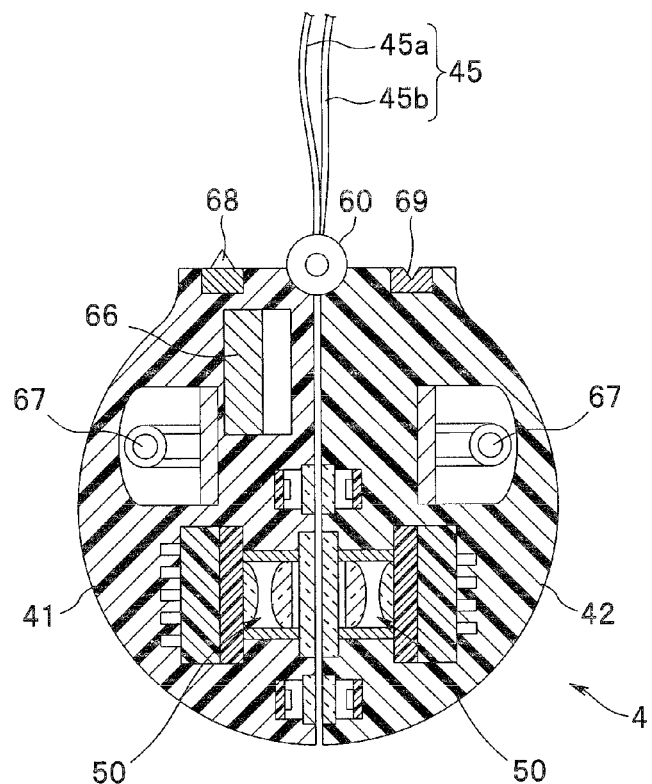
FIG. 27 is a sectional view of a configuration of an intra-abdominal cavity set camera according to a fifth modification of the first embodiment in which two image pickup sections are provided.
Figure 28:
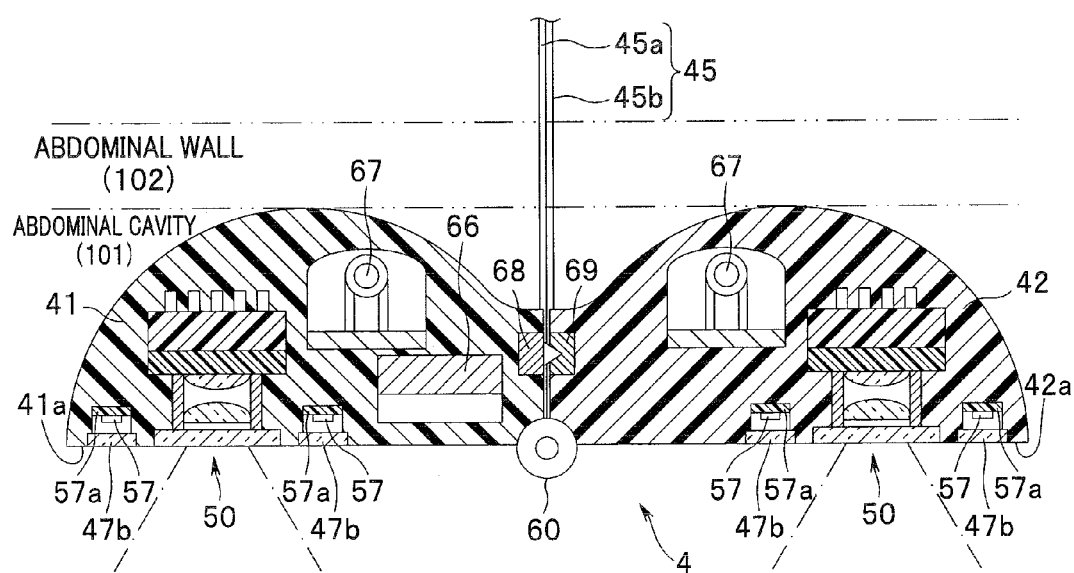
FIG. 28 is a sectional view of a photographable state in which the intra-abdominal cavity set camera shown in FIG. 27 according to the fifth modification is opened.
Figure 29:
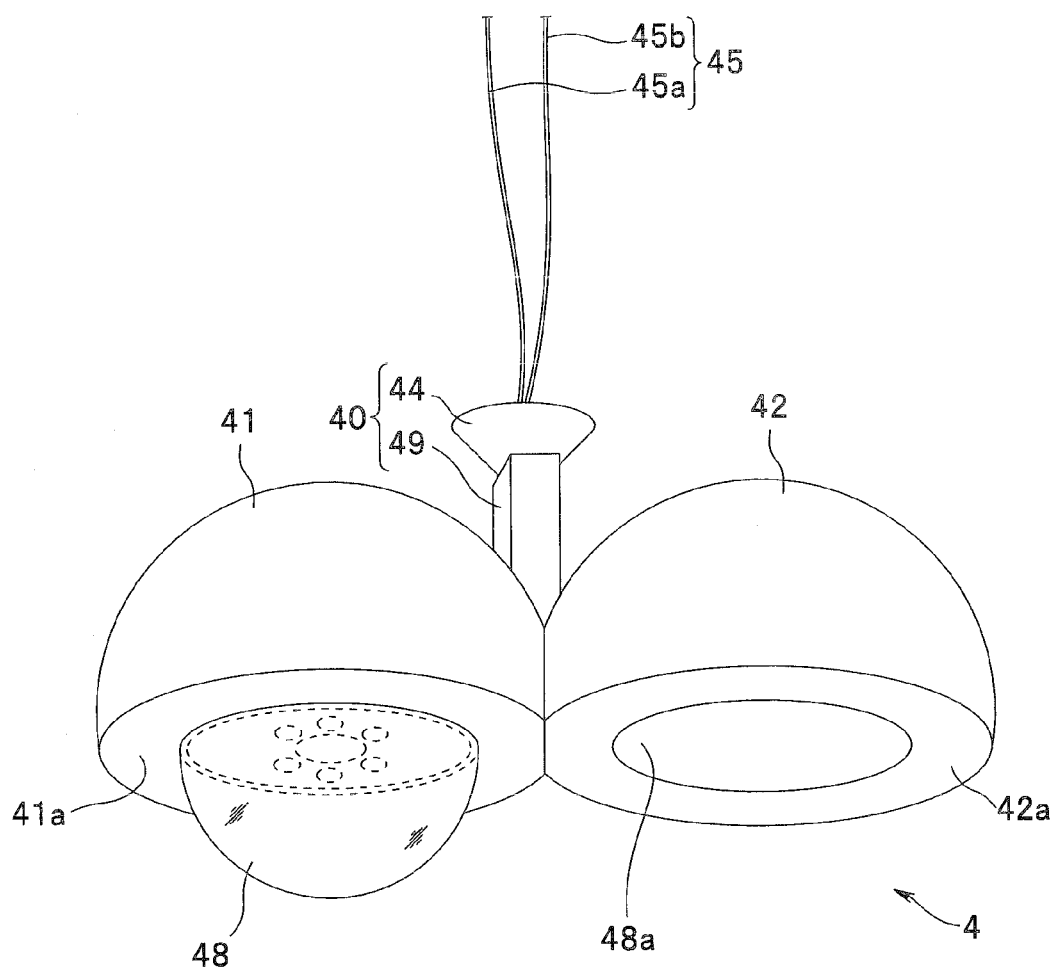
FIG. 29 is a perspective view of a configuration of an intra-abdominal cavity set camera according to a sixth modification of the first embodiment in which a dome-like transparent cover is provided in one of divided surfaces on which an image pickup section and an illumination unit are provided, respectively.
Figure 30:
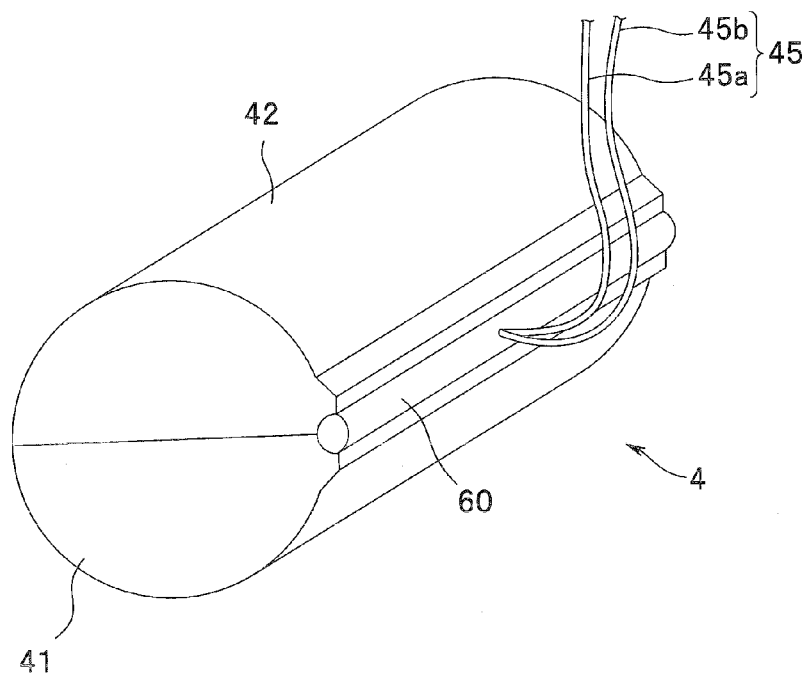
FIG. 30 is a perspective view of an example of an intra-abdominal cavity set camera according to a seventh modification of the first embodiment, an external shape of which is a substantial columnar shape.
Figure 31:
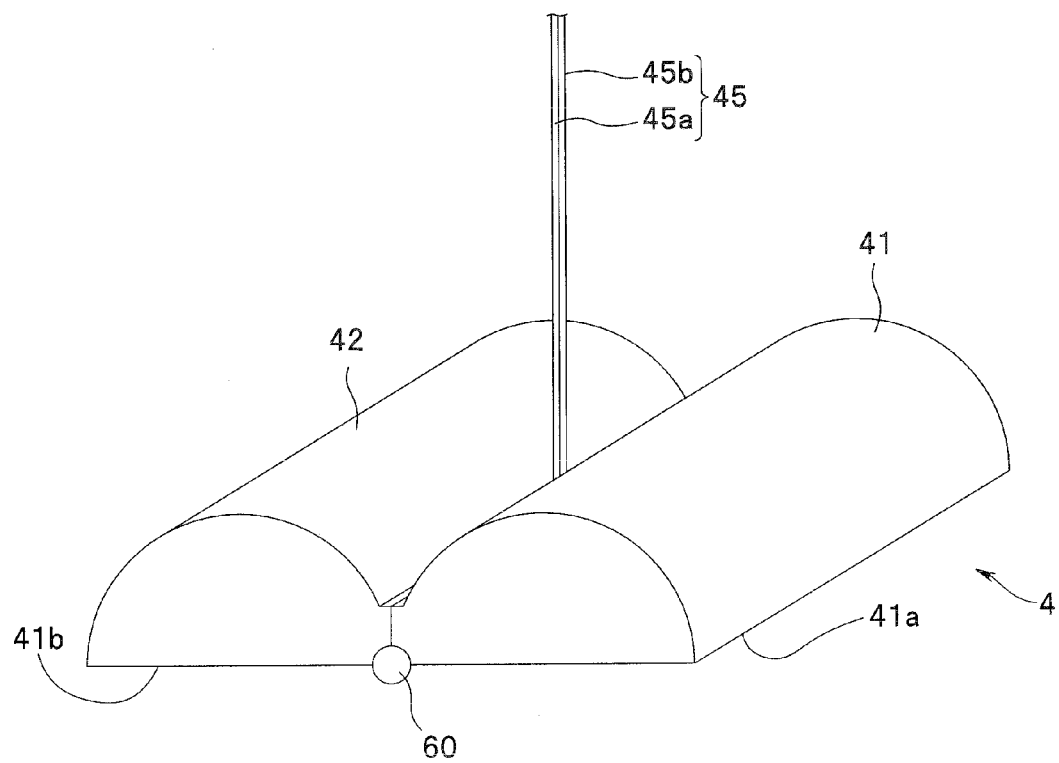
FIG. 31 is a perspective view of a photographable state in which the intra-abdominal cavity set camera shown in FIG. 30 according to the seventh modification is opened.
Figure 32:
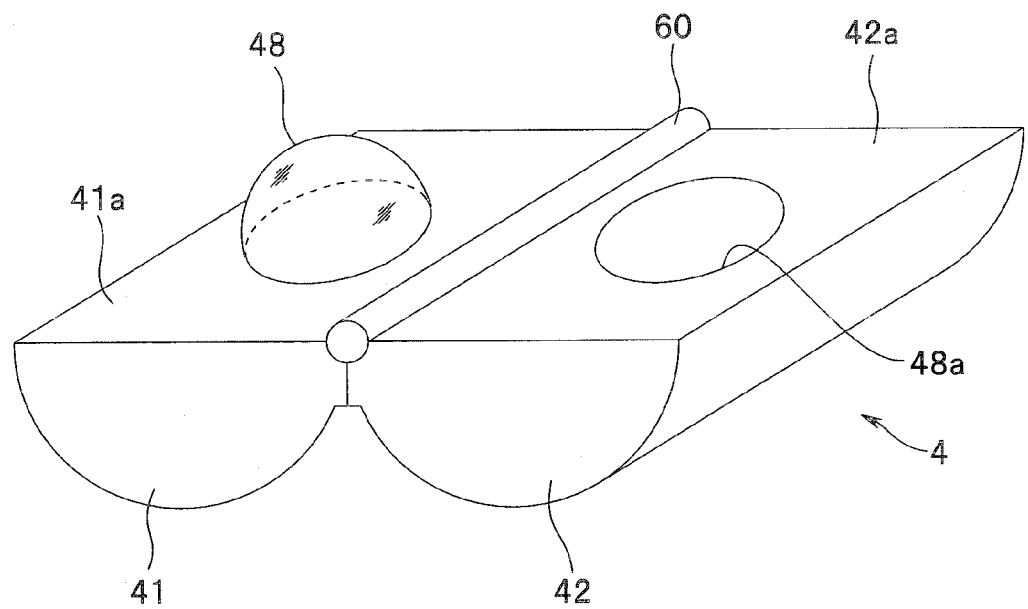
FIG. 32 is a perspective view of a configuration of the intra-abdominal cavity set camera shown in FIG. 30 according to the seventh modification in which a dome-like transparent cover is provided on a divided surface.

First, an endoscope system as a medical apparatus according to the present invention used in the laparoscopic surgical operation is explained below. FIGS. 1 to 32 relates to a first embodiment of the present invention. FIG. 1 is a diagram of a configuration of the endoscope system as the medical apparatus. FIG. 2 is a sectional view of a configuration of an external device. FIG. 3 is a sectional view of an action of a penetrating needle of the external device. FIG. 4 is a perspective view of a configuration of an intra-abdominal cavity set camera. FIG. 5 is an exploded perspective view of the configuration of the intra-abdominal cavity set camera. FIG. 6 is a sectional view of a state in which the intra-abdominal cavity set camera is closed. FIG. 7 is a sectional view of a state in which the intra-abdominal cavity set camera is fixed to the abdominal wall and opened. FIG. 8 is a plan view of a layout of an observation window and illumination windows of the intra-abdominal cavity set camera. FIG. 9 is a plan view of a layout of an observation window and an illumination window of an intra-abdominal cavity set camera according to a first modification of the first embodiment. FIG. 10 is a diagram of a state in which trocars are penetrated into the abdominal wall of a patient. FIG. 11 is a diagram for explaining a procedure for leading the intra-abdominal cavity set camera into the abdominal cavity. FIG. 12 is a diagram of a state in which a hook needle is penetrated into the abdominal wall and a wire bundle of the intra-abdominal cavity set camera is hooked and for explaining a procedure for leading the intra-abdominal cavity set camera into the abdominal cavity. FIG. 13 is a diagram of a state in which the hook needle that hooks the wire bundle of the intra-abdominal cavity set camera is pulled up and for explaining a procedure for fixing the intra-abdominal cavity set camera to the abdominal wall. FIG. 14 is a diagram of a state in which the hook needle is pulled up and a fixing unit is lowered along the hook needle and for explaining a procedure for fixing the intra-abdominal cavity set camera to the abdominal wall. FIG. 15 is a sectional view for explaining an action of the external device. FIG. 16 is a diagram of a state in which the fixing unit is set on the abdomen and the intra-abdominal cavity set camera is fixed to the abdominal wall. FIG. 17 is a sectional view of the fixing unit and the intra-abdominal cavity set camera in the state shown in FIG. 16. FIG. 18 is an overall diagram of the endoscope system in a state in which the intra-abdominal cavity set camera is fixed to the abdominal wall. FIG. 19 is a sectional view of a configuration of an intra-abdominal cavity set camera according to a second modification of the first embodiment in which a switch for controlling ON and OFF of an electric function is provided. FIG. 20 is a sectional view of a configuration of the intra-abdominal cavity set camera shown in FIG. 19 according to the second modification in which the switch for controlling ON and OFF of the electric function is changed to an optical sensor. FIG. 21 is a side view of an intra-abdominal cavity set camera according to a third modification in a closed state. FIG. 22 is a diagram of a state in which the intra-abdominal cavity set camera shown in FIG. 21 is fixed to the abdominal wall. FIG. 23 is a sectional view of an abdominal wall fixing unit of the intra-abdominal cavity set camera shown in FIG. 22. FIG. 24 is a plan view of the intra-abdominal cavity set camera shown in FIG. 23 viewed from an arrow XXIV direction. FIG. 25 is a perspective view of a configuration of an intra-abdominal cavity set camera according to a fourth modification of the first embodiment in which an opening button is provided in a hinge mechanism. FIG. 26 is a perspective view of an opening action of the intra-abdominal cavity set camera shown in FIG. 25. FIG. 27 is a sectional view of a configuration of an intra-abdominal cavity set camera according to a fifth modification of the first embodiment in which two image pickup sections are provided. FIG. 28 is a sectional view of a photographable state in which the intra-abdominal cavity set camera shown in FIG. 27 is opened. FIG. 29 is a perspective view of a configuration of an intra-abdominal cavity set camera according to a sixth modification of the first embodiment in which a dome-like transparent cover is provided in one of divided surfaces on which an image pickup section and an illumination unit are provided, respectively. FIG. 30 is a perspective view of an example of an intra-abdominal cavity set camera according to a seventh modification of the first embodiment, an external shape of which is a substantial columnar shape. FIG. 31 is a perspective view of a photographable state in which the intra-abdominal cavity set camera shown in FIG. 30 is opened. FIG. 32 is a perspective view of a configuration of the intra-abdominal cavity set camera shown in FIG. 30 in which a dome-like transparent cover is provided on a divided surface.

As shown in FIG. 1, an endoscope system 1 according to the present embodiment that performs the laparoscopic surgical operation mainly includes a rigid endoscope 2 as a first photographing device, an external device 3, an intra-abdominal cavity set camera (hereinafter abbreviated as camera) 4, which is an extremely small medical apparatus, as a second photographing device and an image pickup apparatus, a light source device 5, a camera control unit (hereinafter abbreviated as CCU) 6 as a signal processing unit incorporating an image processing circuit, and a display device 7 that is connected to the CCU 6 by a communication cable 13 and displays an observation image.

The light source device 5 supplies illumination light to an illumination optical system included in the rigid endoscope 2. The light source device 5 and the rigid endoscope 2 are detachably connected by a light source cable 10.

The rigid endoscope 2 mainly includes a rigid insertion portion 8 and an operation portion 9 connected to a proximal end portion of the insertion portion 8. An image guide and a light guide bundle are inserted through the inside of the insertion portion 8 of the rigid endoscope 2. A photographing optical system that condenses light of a subject image on a camera for rigid endoscope explained later via the image guide and an illumination optical system that irradiates illumination light from the light guide bundle to the subject are disposed on a distal end surface of the insertion portion 8.

The operation portion 9 of the rigid endoscope 2 incorporates a not-shown camera head in which a solid-state image pickup device such as a CCD or a CMOS is arranged. An optical image of an observed region illuminated by the illumination light supplied from the light source device 5 to the rigid endoscope 2 via the light source cable 10 is picked up by the camera head in the operation portion 9 via the image guide of the insertion portion 8. The camera for rigid endoscope photoelectrically converts the picked-up optical image into an image signal. The image signal is transmitted to the CCU 6 via an image pickup cable 11. An image pickup optical system is set in the rigid endoscope 2 according to the present embodiment such that a photographable angle of view $\alpha$ thereof (see FIG. 18) is, for example, 70° to 75°.

The CCU 6 generates the transmitted image signal as a video signal and outputs the video signal to the display device 7. The display device 7 is, for example, a liquid crystal display. The display device 7 receives the video signal output from the CCU 6 and displays a normal observation image formed by the rigid endoscope 2 and a wide angle observation image formed by the camera 4 on a screen as multi-two-screen display or individually displays the images in a switching manner. The CCU 6 is detachably connected to a fixing unit 15 of the external device 3 explained later by an electric cable 12.

The external device 3 is explained in detail with reference to FIGS. 2 and 3.

As shown in FIGS. 2 and 3, the external device 3 includes the fixing unit 15 that tugs and fixes the camera 4 in the body cavity and a hook needle 16 as a penetrating needle that hooks and pulls up the camera 4.

The fixing unit 15 incorporates, in a housing 21 formed of a nonmagnetic material, a receiver 22 and an electric connector unit 23 electrically connected to the receiver 22. The electric connector unit 23 is connected to the electric cable 12 connected to the CCU 6. The fixing unit 15 transmits power supply from the CCU 6 and a signal from the receiver 22 to the CCU 6 via the electric cable 12.

A slide hole 24 is formed in the housing 21 in a lateral direction from a side thereof. A wire fixing lever 26 configuring a fixing section, on an end face of which an urging spring 25 is fixed and which is formed of a nonmagnetic material, is inserted through and arranged in the slide hole 24. The wire fixing lever 26 is formed in a substantially rectangular parallelepiped shape and disposed slidably along the slide hole 24 in an inner direction of the housing 21. A hole 27 having a convex arcuate surface 27a on the urging spring 25 side is formed halfway in the wire fixing lever 26.

A wire inserting-through section 28 vertically piercing through the housing 21 is formed in the housing 21. In the wire inserting-through section 28, a conical taper surface 29 is formed to expand to an upper part serving as an opening in an upper surface of the housing 21.

In the fixing unit 15 configured as explained above, the hook needle 16 is inserted through and arranged in a hole, which pierces through the fixing unit 15 in the vertical direction, to be freely inserted and pulled in a slide position where the wire fixing lever 26 is pushed in the housing 21 such that the hole 27 of the wire fixing lever 26 and the wire inserting-through section 28 coincide with each other.

The hook needles 16 of the external device 3 includes a cylindrical penetrating needle tube 31, a needle head 32 connected to an upper part of the penetrating needle tube 31, a penetrating rod 33 having a hook section 34, which is slidably inserted through the penetrating needle tube 31, formed at a distal end portion thereof, a hook head 35 connected to an upper part of the penetrating rod 33, and a spring 36 interposed between the hook head 35 and the needle head 32.

The penetrating needle tube 31 is an elongated metal pipe of about 3 mm in diameter formed in a sharp needle shape cut at a distal end portion thereof. The needle head 32 has an outer diameter larger than that of the penetrating needle tube 31 and is formed in a conical shape on a distal end side and integrally formed with the penetrating needle tube 31. The needle head 32 comes into contact with a taper surface 29 formed in an upper part of the housing 21 to prevent the hook needle 16 from coming off downward in the housing 21.

The penetrating rod 33 is an elongated metal bar. In the penetrating rod 33, the hook head 35 connected to the upper part thereof is urged in a direction away from the needle head 32 by the spring 36. Consequently, in the penetrating rod 33, the hook section 34 formed at the distal end portion is housed in the penetrating needle tube 31.

In the hook needle 16, when the hook head 35 is pushed into the penetrating needle pipe 31 by a user against the urging force of the spring 36 (as indicated by an arrow F in FIG. 3), the hook section 34 formed at the distal end portion projects from the distal end portion of the penetrating needle pipe 31.

The wire fixing lever 26 is inserted through and fixed in the housing 21 by the pressing force in an outer side direction of the housing 21 caused by the urging force of the urging spring 25 in a state in which the hook needle 16 configured in this way is inserted through and arranged in the wire inserting-through section 28 of the housing 21 and the hole 27 of the wire fixing lever 26. In other words, an outer circumferential surface of the penetrating needle tube 31 is pressed by the arcuate surface 27a formed on one side of the hole 27 of the wire fixing lever 26 and comes into contact with an inner surface of the wire inserting-through section 28, whereby the hook needle 16 is fixed in a state inserted through the housing 21.

The camera 4 as the medical apparatus according to the present embodiment is explained in detail with reference to FIGS. 4 to 9.

As shown in FIGS. 4 to 7, the camera 4 includes two semispherical armor units (which may be hereinafter referred to as first and second armor units) 41 and 42 that are openable and closable. In an unphotographable state in which a first divided surface 41a and a second divided surface 42a as plane sections of the respective two armor units 41 and 42 are closed to be opposed to and come into contact with each other and are formed in a substantial spherical shape, the camera 4 is in a covered state in which image pickup means as an image pickup section is covered. In other words, the first armor unit 41 and the second armor unit 42 configure covering means as a covering section, which covers the image pickup means explained later, with the first divided surface 41a and the second divided surface 42a set in substantial surface contact with each other.

The camera 4 can be changed to a photographable state in which the first armor unit 41 and the second armor unit 42 pivot in opposite directions around a supporting shaft 49a of an abdominal wall fixing unit 40, which is holding means as a holding section, and the first divided surface 41a and the second divided surface 42a separate from each other and open to be included in substantially the same plane (see FIG. 7).

The first armor unit 41 configures a camera unit as an image pickup section. The first armor unit 41 includes an image pickup unit 50 of the image pickup section as image pickup means, and plural illumination units 57 configuring a small and low-power-consumption illumination unit including LEDs, organic ELs, or the like as light sources of illumination light.

The image pickup unit 50 mainly includes a solid-state image pickup device 55 such as a CCD or a CMOS, an image pickup device driving circuit unit 55a that controls to drive the solid-state image pickup device 55 and photoelectrically converts photographing light made incident on the solid-state image pickup device 55, an object lens group 56 that condenses the photographing light on the solid-state image pickup device 55, and a lens holding frame 56a that holds the object lens group 56.

The illumination units 57 are arranged on an illumination driving circuit unit 57a controlled to be driven. Cover members 47a and 47b formed by sapphire glass or the like configuring transparent observation window and illumination windows that hermetically seal and cover the image pickup unit 50 and the illumination units 57 are disposed on the first divided surface 41a of the first armor unit 41.

In the image pickup unit 50 provided in the first armor unit 41 as the camera unit according to the present embodiment, an image pickup optical system that picks up images in a wide-angle field of view range is set such that a photographable angle of view $\beta$ (see FIG. 18) thereof is, for example, equal to or larger than 90°.

On the other hand, the second armor unit 42 incorporates a transmitter 67 as one auxiliary function device configuring an auxiliary function incorporated gripping unit in the present embodiment and used for transmitting an image signal from the image pickup unit 50 in the first armor unit 41 to the outside by radio and a battery 66 configuring a power supply unit as the other auxiliary function device for performing power feed to the image pickup unit 50, the illumination units 57 as the illumination unit, and the illumination driving circuit unit 57a. The image signal photoelectrically converted by the image pickup unit 50 is transmitted from the transmitter 67 to the receiver 22 (see FIGS. 2 and 3) disposed in the housing 21 of the external device 3 by radio.

In the first armor unit 41 and the second armor unit 42, hook-like pivoting supports 52 are integrally formed in portions along the respective first divided surface 41a and second divided surface 42a. Grooves 52a are formed in the centers along the thickness direction of the pivoting supports 52 in order to insert wires 45a and 45b through the pivoting supports 52.

The abdominal wall fixing unit 40 of the camera 4 includes a supporting member 49 in which the supporting shaft 49a is suspended in a recess formed at one end portion and a suction cup 44 fixed to the other end face of the supporting member 49. In the abdominal wall fixing unit 40, the pivoting supports 52 formed in the respective first armor units 41 and second armor units 42 are hooked on the supporting shaft 49a of the supporting member 49. This allows the first armor unit 41 and the second armor unit 42 of the camera 4 to freely pivot.

A not-shown torsion spring that urges the first divided surface 41a of the first armor unit 41 and the second divided surface 42a of the second armor unit 42 in a contacting direction is provided in the supporting shaft 49a of the abdominal wall fixing unit 40. Predetermined urging force is applied to the camera 4 by the torsion spring in a direction for bringing the first armor unit 41 and the second armor unit 42 into the closed unphotographable state.

Plane sections 51 are respectively formed near the pivoting supports 52 in the first armor unit 41 and the second armor unit 42. The first armor unit 41 and the second armor unit 42 have recesses 51a, which house a one end portion of the supporting member 49 of the abdominal wall fixing unit 40, around the pivoting supports 52. When the first armor unit 41 and the second armor unit 42 pivot around the supporting shaft 49a in directions separating from each other, the plane sections 51 come into contact with substantial surface contact with each other in a position where the first divided surface 41a and the second divided surface 42a are within substantially the same plane.

Contact plane sections 51b are formed in the first armor unit 41 and the second armor unit 42 to have steps from the recesses 51a. The contact plane sections 51b pivot around the supporting shaft 49a in a direction in which the contact plane sections 51b separate from each other and come into surface contact with the pivoting supports 52 in the position where the first divided surface 41a and the second divided surface 42a are within substantially the same plane.

One ends of two pull-up wires 45a and 46b having predetermined length are connected to bottom surfaces of the recesses 51a of the first armor unit 41 and the second armor unit 42 by fixing section 45c (see FIG. 6). The wires 45a and 45b configure a pair of wire bundles 45. One wire bundle 45 is coupled to the first armor unit 41 and the other is coupled to the second armor unit 42.

The wire 45a on the first armor unit 41 side is inserted through the groove 52a formed in the pivoting support 52 of the second armor unit 42. The wire 45b on the second armor unit 42 side is inserted through the groove 52a formed in the pivoting support 52 of the first armor unit 41. After being inserted through a hole 49b formed in the supporting member 49, the wires 45a and 45b are individually inserted through two holes 44a formed in the suction cup 44 and arranged to extend out from the surface of the suction cup 44.

As a layout of the cover member 47a as the observation window and the cover members 47b as the illumination windows provided on the divided surface 41a of the first armor unit 41, as shown in FIG. 8, plural (six in the present embodiment) cover members 47b for illumination are provided at equal intervals around the cover member 47a for observation provided substantially in the center.

The image pickup unit 50 and the illumination units 57 of the first armor unit 41 and the battery 66 and the transmitter 67 of the second armor unit 42 are electrically connected by a not-shown cable.

First Modification

As shown in FIG. 9, the cover member 47a for observation may be provided substantially in the center of the divided surface 41a of the first armor unit 41 and the cover member 47b for illumination may be provided substantially in the center of the divided surface 42a of the second armor unit 42. In the case of such a configuration, the illumination unit 57 as the illumination unit including the LED or the organic EL as the light source of illumination light is disposed in the second armor unit 42. The cover members 47b as the illumination windows may be an illumination unit of a surface light source including an LED or an organic EL.

The endoscope system 1 according to the present embodiment configured as explained above is used for the laparoscopic surgical operation and used for treatment in the inside of the abdominal cavity that is one of body cavities of a patient.

A procedure for setting the endoscope system 1 according to the present embodiment in the abdominal cavity as the body cavity of the patient for the laparoscopic surgical operation and an action of the endoscope system 1 are explained in detail below with reference to FIGS. 10 to 18.

First, a surgeon cuts small dissected portions in two places of an abdominal wall 102 of a patient 100 using a knife or the like. As shown in FIG. 10, the surgeon penetrates trocars 110 and 111 in the dissected portions. For example, the surgeon cuts the abdominal wall 102 in another place (position) a predetermined distance away from the trocar 110 for leading the rigid endoscope 2 into an abdominal cavity 101 and penetrates, into the abdominal cavity 101, the trocar 111 for leading a treatment instrument 120 such as grasping forceps into the abdominal cavity 101.

As shown in FIGS. 2 and 3, the surgeon inserts the penetrating needle tube 31 of the hook needle 16 into the wire inserting-through section 28 provided in the fixing unit 15 of the external device 3. In inserting the penetrating needle tube 31, the surgeon pushes the wire fixing lever 26 into the housing 21 such that the penetrating needle tube 31 pierces through the fixing unit 15. The surgeon inserts the penetrating needle tube 31 such that the penetrating needle tube 31 pierces through the hole 27 of the wire fixing lever 26.

The surgeon locates the fixing unit 15 sufficiently on the needle head 32 side on the front side of the penetrating needle tube 31 and sufficiently projects the penetrating needle tube 31 from the bottom surface of the fixing unit 15 (see FIGS. 2 and 3). In this state, the fixing unit 15 does not come off from the penetrating needle tube 31 because the arcuate surface 27a as one wall surface of the hole 27 of the wire fixing lever 26 comes into contact with and holds the penetrating needle tube 31 with the urging force of the urging spring 25.

Subsequently, the surgeon inserts the insertion portion 8 of the rigid endoscope 2 into the abdominal cavity 101 via the trocar 110 (see FIG. 11). The surgeon inserts the camera 4 grasped by the treatment instrument 120 such as the grasping forceps into the abdominal cavity 101 via the other trocar 111. It is advisable that the surgeon inserts the camera 4 into the abdominal cavity 101 while checking an image formed by the rigid endoscope 2.

When the camera 4 is led into the abdominal cavity 101 via the trocar 111, the abdominal wall fixing unit 40 or the base of the wire bundle 45 is nipped and grasped by a treating section 121 of the treatment instrument 120 such as the grasping forceps. Since the camera 4 is a substantial sphere, when the camera 4 is led into the abdominal cavity, the camera 4 is easily inserted into the trocar 111. In other words, the surgeon can easily lead the camera 4 into the abdominal cavity 101 such that the camera 4 is not caught by the trocar 111. Further, since the camera 4 is the substantial sphere, even if the camera 4 touches a body tissue when the camera 4 is led into the abdominal cavity 101 of the patient, the camera 4 can be led into the abdominal cavity 101 in a non-invasive manner.

As shown in FIGS. 11 to 12, the surgeon penetrates the penetrating needle tube 31 of the hook needle 16 inserted and held in the fixing unit 15, which configures the external device 3, while checking an image formed by the rigid endoscope 2 such that the penetrating needle tube 31 pierces through the abdominal wall 102. As shown in FIG. 12, the surgeon pushes the hook head 35 in a direction indicated by an arrow F in the figure in order to lead out the penetrating rod 33 from the penetrating needle tube 31. From this state, the surgeon hooks the hook section 34 formed in the penetrating rod 33 on the wire bundle 45 including the two wires 45a and 45b of the camera 4 while looking at an image formed by the rigid endoscope 2.

When the wire bundle 45 is hooked on the hook section 34, the surgeon releases the push-in of the hook head 35 of the penetrating rod 33. Then, the penetrating rod 33 is led into the penetrating needle tube 31 in a state in which the wire bundle 45 is hooked on the hook section 34.

Thereafter, as shown in FIG. 13, the surgeon pulls the penetrating needle tube 31 of the hook needle 16 from the abdominal cavity 101 to the outside of the body (in an UP direction in the figure) in a state in which the wire bundle 45 is hooked on the hook section 34 of the penetrating rod 33. As shown in FIG. 14, the surgeon pulls the penetrating needle tube 31 of the hook needle 16 from the abdominal cavity 101, moves the fixing unit 15 in an abdomen direction of the patient 100 (a DOWN direction in the figure) relatively to the penetrating needle tube 31, and tugs the penetrating needle tube 31 until the wire bundle 45 is pierced through the wire inserting-through section 28 of the fixing unit 15.

When the surgeon tugs the penetrating needle tube 31, the surgeon can easily slide the fixing unit 15 relatively to the penetrating needle tube 31 of the hook needle 16 by pushing the wire fixing lever 26 of the fixing unit 15 to an inner side of the housing 21 (an arrow P direction in FIG. 15). When the wire bundle 45 is pierced through the wire inserting-through section 28 of the fixing unit 15, as shown in FIG. 15, the surgeon moves the fixing unit 15 relatively to the wire bundle 45 in the abdomen direction (the DOWN direction in the figure) while tugging the wire bundle 45 itself including the two wires 45a and 45b (in the UP direction in the figure).

In other words, the surgeon can easily slide the fixing unit 15 relatively to the penetrating needle tube 31 of the hook needle 16 and the wire bundle 45 of the camera 4 by maintaining a state in which the wire fixing lever 26 of the fixing unit 15 is pushed into the inner side of the housing 21.

The surgeon tugs the wire bundle 45 of the camera 4 until the fixing unit 15 and the camera 4 hold the abdominal wall 102 in a state in which the fixing unit 15 is place on the abdomen of the patient 100 as shown in FIG. 16. Then, in the camera 4, the suction cup 44 of the abdominal wall fixing unit 40 comes into contact with and adheres to the abdominal wall 102. Reaction is caused in the first armor unit 41 and the second armor unit 42 by the tug of the wire bundle 45 via the abdominal wall fixing unit 40. The first divided surface 41a and the second divided surface 42a of the respective armor units open in directions away from each other against the urging force of the torsion spring.

When the surgeon confirms from an image formed by the rigid endoscope 2 that, as shown in FIG. 17, the camera 4 comes into contact with the inner surface of the abdominal wall 102 and the first armor unit 41 and the second armor unit 42 open, the surgeon releases the push-in of the wire fixing lever 26 of the fixing unit 15.

Then, the wire fixing lever 26 of the fixing unit 15 receives the urging force of the urging spring 25 and moves in an arrow R direction shown in FIG. 17. The hole 27 shifts from the wire inserting-through section 28 of the housing 21. The bundle 45 inserted through the hole 27 and the wire inserting-through section 28 is nipped and fixed to the housing 21. Tension equal to or larger than a fixed strength is always applied to the wire bundle 45 of the camera 4. Consequently, the tension equal to or larger than the fixed strength applied to the wire bundle 45 is always maintained and the fixing unit 15 and the camera 4 are maintained and fixed in a state in which the fixing unit 15 and the camera 4 hold the abdominal wall 102. The camera 4 is maintained in a state in which the first armor unit 41 and the second armor unit 42 are open. In this way, in the camera 4, the pivoting supports 52 of the first armor unit 41 and the second armor unit 42 are hooked on the supporting shaft 49a of the abdominal wall fixing unit 40 and the wires 45a and 45b are tugged. The cover members 47a and 47b configuring the covered observation window and illumination windows can be exposed by a field-of-view control section as field-of-view controlling means opened by the first armor unit 41 and the second armor unit 42.

In this way, as shown in FIG. 18, the camera 4 is set in the abdominal cavity 101 of the patient 100 in a surely stable state. The laparoscopic surgical operation is performed by the endoscope system 1 according to the present embodiment. For example, one end of a not-shown pneumoperitoneum tube is attached to the trocar 110 and, for example, a carbon dioxide gas is injected into the abdominal cavity 101 as gas for pneumoperitoneum for the purpose of securing a field of vision of the rigid endoscope 2 and for the purpose of securing an area for operating an operation instrument and the like. The surgeon inserts the rigid endoscope 2 into the trocar 110 and inserts the treatment instrument 120 into the trocar 111 to perform the laparoscopic surgical operation in a state in which the camera 4 is placed in the abdominal cavity 101 to be caused to adhere to the abdominal wall 102.

When the surgeon finishes the laparoscopic surgical operation, the surgeon pulls the fixing unit 15 from the wire bundle 45 while pushing the wire fixing lever 26 of the fixing unit 15 to the inner side of the housing 21. The surgeon grasps the camera 4 in the abdominal cavity 101 with the treatment instrument 120 such as the grasping forceps and takes out the camera 4 to the outside from the abdominal cavity 101 via the trocar 111.

With the endoscope system 1 according to the embodiments explained above, it is possible to observe the body tissue inside the body cavity, i.e., the abdominal cavity 101 in multiple viewpoints including a wide angle. For example, an entire excision line in an operation of a large organ or excision of the large intestine can be easily grasped. With the endoscope system 1, when the small camera 4 led into the abdominal cavity 101 separately from the rigid endoscope 2 for enlarged observation is set, it is possible to perform a low-invasive surgical operation without increasing burden on a patient. As a result, treatment by the laparoscopic surgical operation is facilitated by using the endoscope system 1 according to the present invention.

When the camera 4 is led into the abdominal cavity 101, the first divided surface 41a of the first armor unit 41 and the second divided surface 42a of the second armor unit 42 are opposed to each other and substantially in surface contact with each other to be closed. Therefore, soil of blood and the like are prevented from adhering to the cover members 47a and 47b serving as the observation window and the illumination windows disposed on the first divided surface 41a of the first armor unit 41.

In particular, even if the camera 4 touches an organ in the abdominal cavity 101, soil such as blood is prevented from adhering to the cover members 47a and 47b serving as the observation window and the illumination windows. Consequently, a field of vision of the image pickup unit 50 is not blocked and irradiation of illumination light is not prevented by the soil such as blood. Therefore, the camera 4 can perform satisfactory observation of a body tissue.

As explained above, the camera 4 as the medical apparatus according to the present invention is the substantial sphere when the camera 4 is led into the body, i.e the abdominal cavity, even if the camera 4 touches a body tissue when the camera 4 is led into the abdominal cavity 101 of the patient 100. Therefore, it is possible to lead the camera 4 into the abdominal cavity 101 in a non-invasive manner. Further, the observation window of the observation optical system and the illumination windows of the illumination optical system are prevented from being soiled so that a field of vision is not deteriorated during use and irradiation of illumination light is not disturbed. Therefore, it is possible to acquire a clear observation image.

It goes without saying that the camera 4 is not limited to the configuration explained above and the first modification and may have configurations explained below.

Second Modification

As shown in FIG. 19, the camera 4 may have a configuration in which, for example, a DIP type switch 70 is provided in the first divided surface 41a of the first armor unit 41 and a main power supply is turned on and off by the switch 70.

Specifically, when the first armor unit 41 and the second armor unit 42 of the camera 4 are closed with the first divided surface 41a and the second divided surface 42a thereof opposed to and close to each other, the switch 70 is depressed by the divided surface 42a of the second armor unit 42. Therefore, the electric function of the camera 4 is turned off. When the first armor unit 41 and the second armor unit 42 of the camera 4 are opened in the photographable state in which the first divided surface 41a and the second divided surface 42a are separated from each other, the depression of the switch 70 is released and the electric function of the camera 4 is turned on.

In other words, in the camera 40, when the switch 70 is turned on and off according to opening and closing of the first armor unit 41 and the second armor unit 42, the supply or the stop of electric power from the battery 66 to the electric devices are executed.

A configuration for performing the supply and the stop of electric power from the battery 66 to the electric devices according to opening and closing of the first armor unit 41 and the second armor unit 42 is not limited to the switch 70. As shown in FIG. 20, optical sensors 71 and 72 such as infrared sensors that detect opening and closing of the first armor unit 41 and the second armor unit 42 may be provided on the first divided surface 41a and the second divided surface 42a, respectively. The optical sensors 71 and 72 are configured to perform the supply and stop of electric power from the battery 66 to the electric devices corresponding to opening and closing of the first armor unit 41 and the second armor unit 42 according to whether light irradiated by one optical sensor 71 is detected by the other optical sensor 72.

With the configuration explained above, the power supply for the camera 4 is turned on only during photographing of a body organ. Therefore, the lifetime of the battery 66 is extended. Moreover, the incorporated battery 66 only has to be a battery corresponding to power feed adjusted to necessary time of use. The battery 66 can be reduced in size. As a result, the camera 4 itself can be reduced in size.

Third Modification

As shown in FIGS. 21 and 22, the first armor unit 41 and the second armor unit 42 are coupled by a hinge mechanism 60 provided in one side portion to be openable and closable. A not-shown urging member such as a spring that urges the first divided surface 41a of the first armor unit 41 and the second divided surface 42a of the second armor unit 42 in contacting directions are incorporated in the hinge mechanism 60.

Ring-like wire connecting sections 41c and 42c to which the wires 45a and 45b are connected, respectively, are provided at vertexes of armor spherical shapes of the first armor unit 41 and the second armor unit 42.

As shown in FIGS. 23 and 24, the abdominal wall fixing unit 40 includes the suction cup 44 and a disc-like supporting member 17, on one side of which the suction cup 44 is fit. Two holes 17a through which the wires 45a and 45b are inserted are formed in the supporting member 17. The two holes 17a have a shape in which a hole diameter on a surface side on the opposite side of the suction cup 44 expands large.

The suction cup 44 and the supporting member 17 are fit with each other such that the two holes 17a communicate with the two holes 44a formed in the suction cup 44. The wires 45a and 45b are inserted through the holes 17a of the supporting member 17 and the holes 44a of the suction cup 44 and extended out from the center of the surface of the suction cup 44.

In a state in which the suction cup 44 adheres to and is in contact with the abdominal wall 102 as shown in FIG. 22, when the two wires 45a and 45b are tugged, the wire connecting sections 41c and 42c of the first armor unit 41 and the second armor unit 42 are pulled to the abdominal wall 102 side. The first armor unit 41 and the second armor unit 42 pivot around a supporting shaft of the hinge mechanism 60. The first divided surface 41a of the first armor unit 41 and the second divided surface 42a of the second armor unit 42 open in directions separating from each other against the urging force of the urging member such as the spring. The camera 4 is brought into a photographable state by the image pickup unit 50.

Fourth Modification

As shown in FIG. 25, the camera 4 may include two opening buttons 60a for opening the first armor unit 41 and the second armor unit 42 at both ends of the hinge mechanism 60 as holding means configuring a holding section that pivots and holds the first armor unit 41 and the second armor unit 42.

When the two opening buttons 60a provided in the hinge mechanism 60 are depressed toward arrow O and O' directions by a treating unit 121 or the like of the treatment instrument 120 such as the grasping forceps, as shown in FIG. 26, the first armor unit 41 and the second armor unit 42 of the camera 4 pivot. The camera 4 is brought into a photographable state in which the first divided surface 41a of the first armor unit 41 and the second divided surface 42a of the second armor unit 42 separate from each other and open.

With such a configuration, the camera 4 can open the first armor unit 41 and the second armor unit 42 at desired time according to operation in the body.

Fifth Modification

As shown in FIGS. 27 and 28, the camera 4 may have a configuration in which image pickup units 50 and plural illumination units 57 as illumination units around the image pickup unit 50 are provided in the first armor unit 41 and the second armor unit 42, respectively.

By providing the two image pickup unit 50 in the camera 4, the camera 4 can be configured to have a function of a stereo camera that can obtain a stereographic image or configured to set photographing ranges by the image pickup units 50 and photograph organs in the abdominal cavity 101 in a wide range.

The camera 4 can also set the image pickup units 50 at a predetermined angle such that photographing directions thereof are apart from each other and photograph organs in the abdominal cavity 101 in a wider range.

With such a configuration, two transmitters 67 for transmitting image signals of the image pickup unit 50 to the outside by radio are provided. The camera 4 may be configured to have one transmitter 67 and transmit image signals of the image pickup units 50 to the outside by radio in a time differential manner or, in the case of the function of the stereo camera, may be configured to convert image signals into a stereographic image and transmit the converted stereographic image signals to the outside by radio.

In the first armor unit 41 and the second armor unit 42, portions coupled by the hinge mechanism 60 are formed as planes. A protrusion member 68 configuring a lock mechanism for locking the photographable state and a concave locking member 69 that locks the protrusion member 68 are provided in the portions formed as planes. For example, the protrusion member 68 and the locking member 69 may be formed of magnets having different poles and hold, with an attractive action of the attracting magnets, the photographable state in which the first armor unit 41 and the second armor unit 42 are open.

Sixth Modification

As shown in FIG. 29, in the camera 4, on the first divided surface 41a of the first armor unit 41 on which the image pickup unit 50 and the illumination units 57 as the illumination units are provided, a dome-like transparent cover 48 that integrally covers the image pickup unit 50 and the illumination unit 57 may be provided. When such a configuration is adopted, in the camera 4, a recess 48a for housing the dome-like transparent cover 48 in the closed state in which the first divided surface 41a of the first armor unit 41 and the second divided surface 42a of the second armor unit 42 are opposed and close to each other is formed on the second divided surface 42a.

Seventh Modification

An external shape of the camera 4 is not limited to the substantial spherical shape and may be, for example, a substantial columnar shape as shown in FIG. 30 as long as a shape of the closed first armor unit 41 and second armor unit 42 can be led into the abdominal cavity 101 via the trocar 111. An external shape of the first armor unit 41 and the second armor unit 42 is a substantial semicolumnar shape obtained by cutting the substantial columnar shape into halves along a longitudinal direction thereof.

One side marginal portions of the first armor unit 41 and the second armor unit 42 are pivotably coupled by the hinge mechanism 60. As shown in FIG. 31, the first divided surface 41a of the first armor unit 41 and the second divided surface 42a of the second armor unit 42 separate from each other and open to be included in substantially the same plane.

It goes without saying that, as shown in FIG. 32, the camera 4 may be configured to provide, on the first divided surface 41a of the first armor unit 41, the dome-like transparent cover 48 that integrally covers the image pickup unit 50 and the illumination unit 57 and form, on the second divided surface 42a of the second armor unit 42, the recess 48a for housing the dome-like transparent cover 48 in the closed state in which the first divided surface 41a of the first armor unit 41 and the second divided surface 42a of the second armor unit 42 are opposed and close to each other.

Second Embodiment

Figure 33:
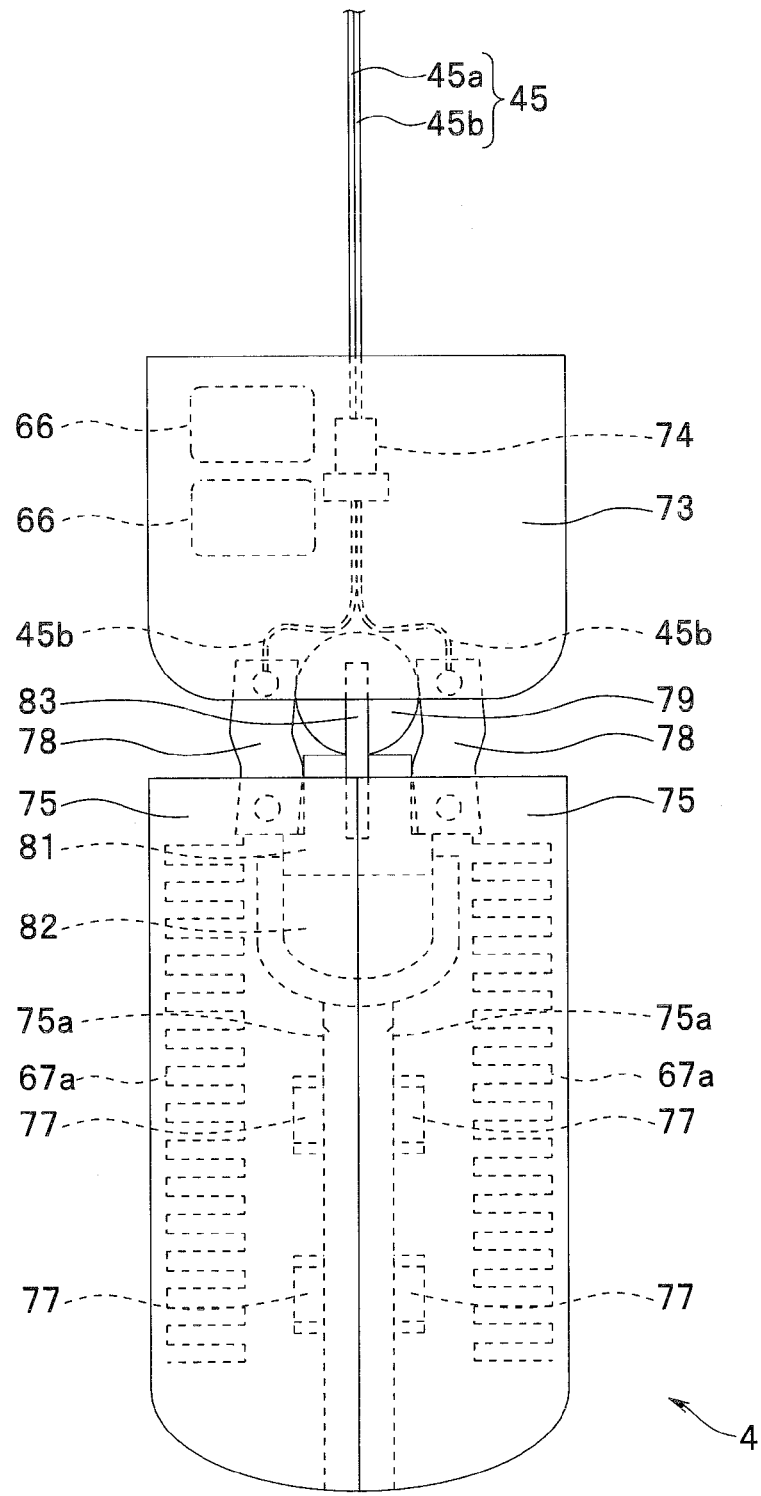
FIG. 33 is a diagram of a state in which an intra-abdominal cavity set camera according to a second embodiment of the present invention is closed.
Figure 34:
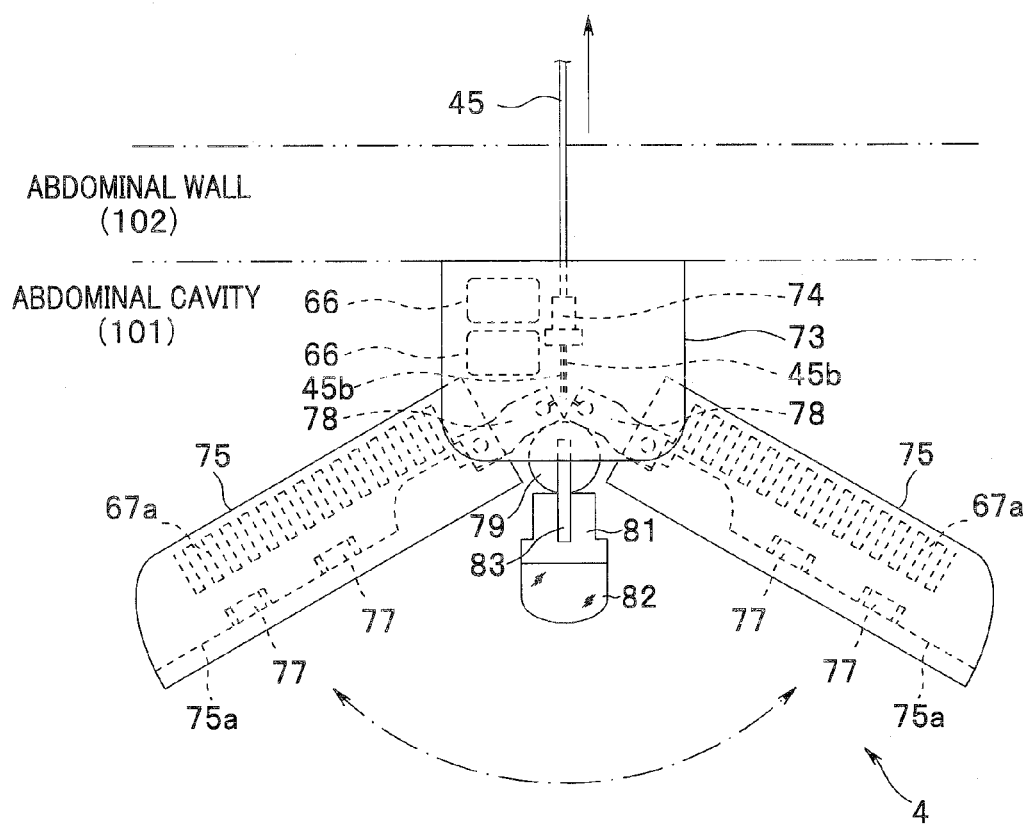
FIG. 34 is a diagram of a state in which the intra-abdominal cavity set camera according to the second embodiment is opened.
Figure 35:
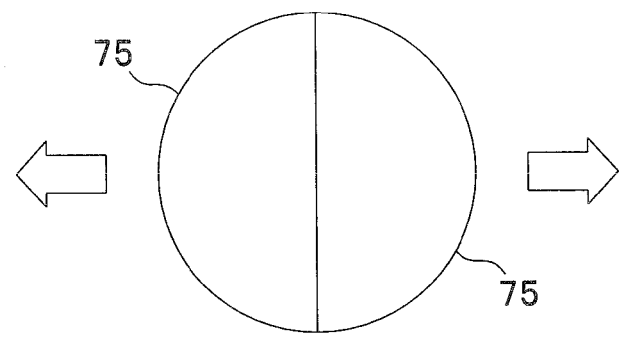
FIG. 35 is a diagram of a configuration of the intra-abdominal cavity set camera according to the second embodiment in which two covers are provided.
Figure 36:
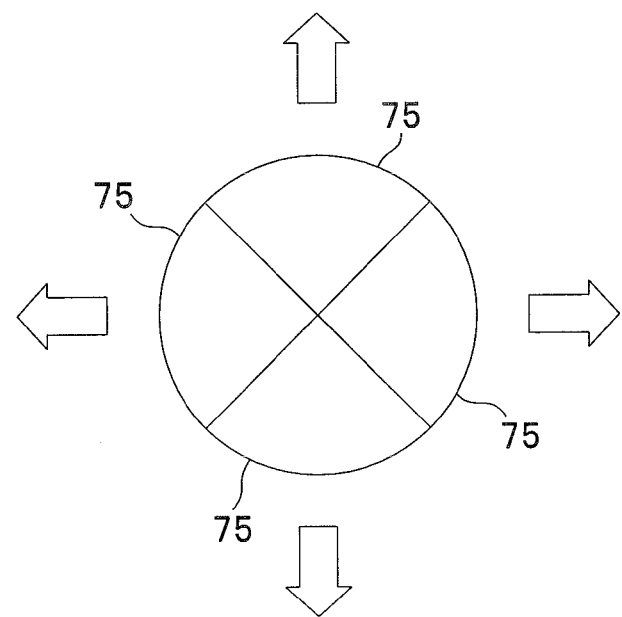
FIG. 36 is a diagram of a configuration of the intra-abdominal cavity set camera according to a modification of the second embodiment in which four covers are provided.
Figure 37:
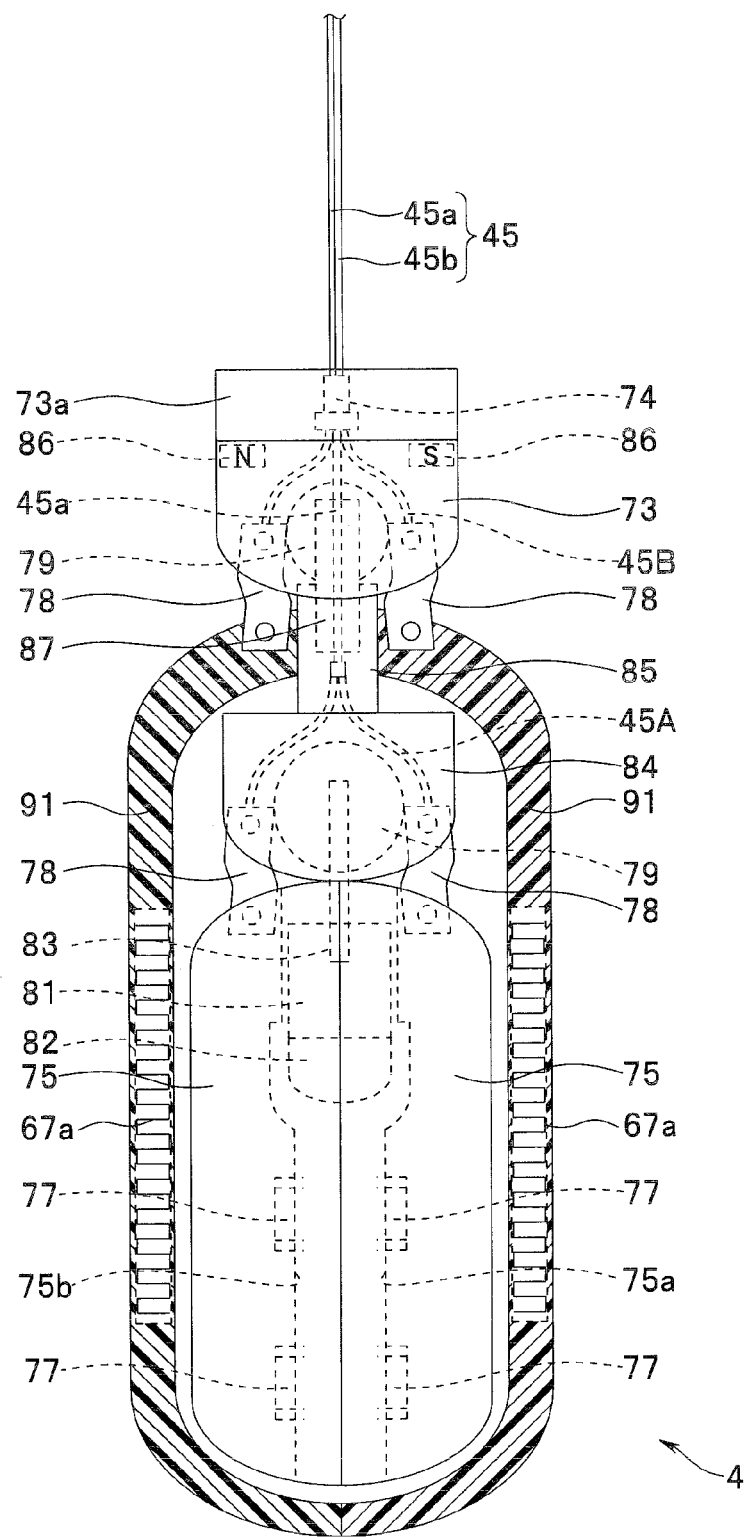
FIG. 37 is a diagram of a state in which the intra-abdominal cavity set camera according to the modification of the second embodiment is closed.
Figure 38:
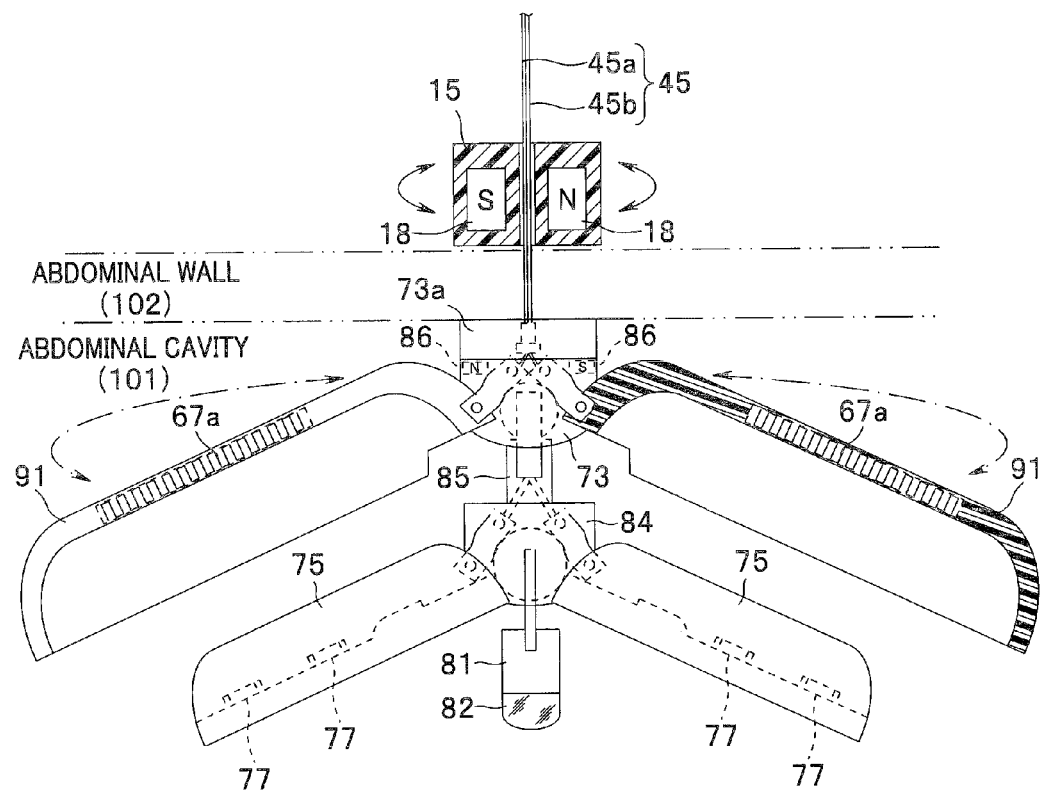
FIG. 38 is a diagram of a state in which the intra-abdominal cavity set camera shown in FIG. 37 according to the modification is opened.

An endoscope system according to a second embodiment of the present invention is explained below with reference to FIGS. 33 to 38. FIGS. 33 to 38 relate to the second embodiment of the present invention. FIG. 33 is a diagram of a state in which an intra-abdominal cavity set camera is closed. FIG. 34 is a diagram of a state in which the intra-abdominal cavity set camera is opened. FIG. 35 is a diagram of a configuration of the intra-abdominal cavity set camera in which two covers are provided. FIG. 36 is a diagram of a configuration of the intra-abdominal cavity set camera in which four covers are provided. FIG. 37 is a diagram of a state in which an intra-abdominal cavity set camera according to a modification is closed. FIG. 38 is a diagram of a state in which the intra-abdominal cavity set camera shown in FIG. 37 is opened.

In the following explanation, components same as those of the endoscope system 1 according to the first embodiment are denoted by the same reference numerals and signs. Detailed explanation of the components is omitted.

As shown in FIGS. 33 and 34, the camera 4 according to the present embodiment mainly includes a block-shaped abdominal wall fixing unit 73, which is holding means as a holding section, a camera main body 81 as an image pickup section, and plural (two in the present embodiment) cover members 75, which is covering means as a covering section, that covers the camera main body 81 in a closed state.

One or plural (two in the present embodiment) batteries 66 and a holding tube 74 through which the wire bundle 45 is inserted and held are provided in the abdominal wall fixing unit 73. The camera main body 81 is fixed to the abdominal wall fixing unit 73 via a supporting member 83. A sphere 79 partially housed in the abdominal wall fixing unit 73 is provided in the supporting member 83.

One ends of link plates 78, plate surfaces of which are S-shaped, are fixed to upper sides of the cover members 75. Antennas 67a are incorporated in the cover members 75 along a longitudinal direction thereof. Plural (two in the present embodiment) illumination units 77 as illuminating means such as LEDs or organic ELs are respectively provided on the divided surface 75a. Not-shown cover members as illumination windows are provided on the surfaces of the illumination units 77.

One ends of the wires 45a and 45b are connected to the other ends of the link plates 78. The antennas 67a configure a transmitter. An image signal picked up by an image pickup section of the camera main body 81 is transmitted to the receiver 22 (see FIGS. 2 and 3) disposed in the housing 21 of the external device 3 by radio.

A not-shown image pickup unit of an image pickup section as image pickup means is provided inside the camera main body 81. A dome-like transparent cover 82 as an observation window is provided to cover the image pickup unit. The batteries 66 of the abdominal wall fixing unit 73 are electrically connected to the image pickup section in the camera main body 81 and the illumination units 77 of the cover members 75 by a not-shown cable. The image pickup section in the camera main body 81 and the antennas 67a of the cover members 75 are connected by a not-shown communication cable.

In the camera 4 according to the present embodiment configured as explained above, as shown in FIG. 34, an upper end face of the abdominal wall fixing unit 73 adheres to the abdominal wall 102. When the wire bundle 45 is tugged in this state, the cover members 75 open. Specifically, when the two link plates 78 provided in the cover members 75 are tugged by the wires 45a and 45b, the link plates 78 move upward and the S-shaped sides set in contact with the surface of the sphere 79 slide to open the cover members 75. In this way, the camera main body 81 covered with the two cover members 75 is exposed and the camera 4 changes to the photographable state.

With the camera 4 according to the present embodiment, as in the first embodiment, it is possible to prevent an observation window of an observation optical system and illumination windows of an illumination optical system from being soiled when the camera 4 is led into the abdominal cavity 101, so that a field of view during use is not deteriorated and irradiation of illumination light is not disturbed, and acquire a clear observation image.

The plural (two in the present embodiment) illumination units 77 are provided on the divided surface 75a of the cover member 75. When the cover member 75 opens, illumination light can be irradiated in a wide range. An angle of the cover members 75 at which the antennas 67a incorporated therein have the test sensitivity can be changed according to an amount of tug of the wires 45a and 45b. Therefore, the directivity of the antenna 67a can be changed to an optimum sensitivity position.

In the present embodiment, as shown in FIG. 35, the two cover members 75 that open to be divided into two are provided. However, the cover members 75 are not limited to this. For example, as shown in FIG. 36, four cover members 75 open to be divided into four may be provided.

As shown in FIGS. 37 and 38, the camera 4 may have a configuration in which the illumination units 77 and the antennas 67a are provided in separate cover members 75 and 91 and the directivity of the antennas 67a can be changed to an optimum position by controlling the cover members 91 to pivot from the outside of the body.

Specifically, the camera 4 includes the cover members (first cover members) 75 that cover the camera main body 81 and include the illumination units 77 and second cover members 91 that further cover the cover member 75 and include the antennas 67a in thick portions thereof.

When the link plates 78 are tugged by wires 45A in the same manner as explained above, the first cover members 75 in this modification move upward and S-shaped sides thereof set in contact with the surface of the sphere 79 provided in a cover holding section 84 slide and open. The wire 45a is divided into plural (two in this modification) wires 45A. Ends of the wires 45A are connected to the link plates 78 of the first cover members 75.

The cover holding section 84 supports and fixes the camera main body 81 via the supporting member 83. The cover holding section 84 is provided on a lower side of the abdominal wall fixing unit 73 and coupled and fixed by a holding tube 85 and a supporting member 87 that supports and fixes the holding tube 85 on the abdominal wall fixing unit 73.

When the link plates 78 are tugged by the wire 45b, the second cover members 91 move upward and S-shaped sides thereof set in contact with the surface of the sphere 79 provided in the abdominal wall fixing unit 73 slide and open. The wire 45b is divided into plural (two in this modification) wires 45B and ends of the wires 45B are connected to the link plates 78 of the second cover members 91.

The abdominal wall fixing unit 73 includes a ring-like magnet 86 in which an N pole and an S pole are magnetized in half areas and an abdominal wall contact member 73a pivotably provided on an upper side. As shown in FIG. 38, a ring-like magnets 18 in which an N pole and an S pole are magnetized in half areas is provided in the fixing unit 15 in this modification.

The S poles and the N poles of the magnet 18 of the fixing unit 15 and the magnet 86 of the abdominal wall fixing unit 73 attract each other. Therefore, when the fixing unit 15 is caused to pivot around the wires 45a and 45b on the abdominal wall 102, the abdominal wall fixing unit 73 pivots following the fixing unit 15 and the second cover members 91 also pivot according to the pivoting of the abdominal wall fixing unit 73.

The cover holding section 84 is fixed to the abdominal wall contact member 73a. Therefore, the first cover members 75 do not pivot and a rotating direction of only the second cover members 91 is changed around the wire bundle 45 according to the pivoting operation of the fixing unit 15 together with the abdominal wall fixing unit 73.

As explained above, the camera 4 according to this modification can change, according to an amount of tug of the wire 45b, an angle of the second cover members 91 to a position where the antennas 67a incorporated therein have the best sensitivity and can change, using the abdominal wall fixing unit 73, the directivity of the antennas 67a around the wires 45a and 45b to an optimum position by controlling the second cover member 91.

Third Embodiment

Figure 39:
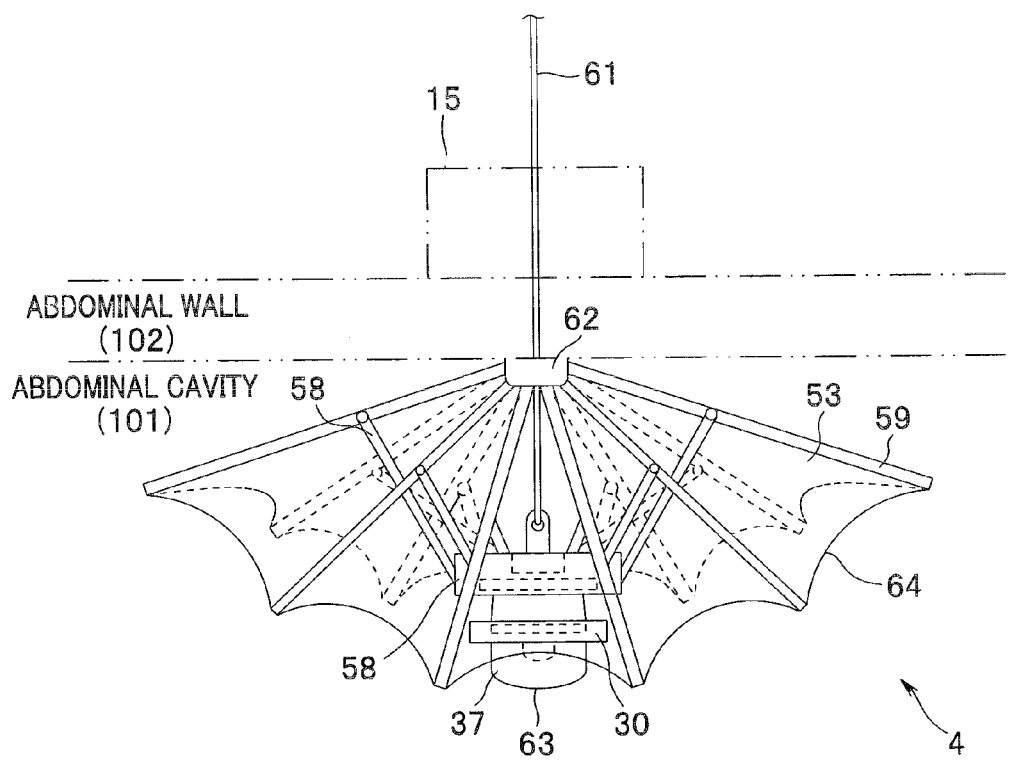
FIG. 39 is a diagram of a state in which an intra-abdominal cavity set camera placed in the abdominal cavity according to a third embodiment of the present invention is opened.
Figure 40:
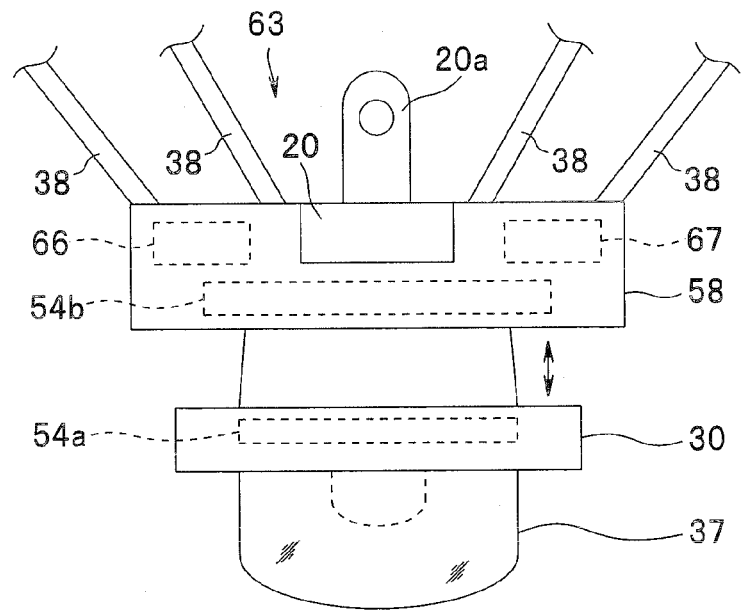
FIG. 40 is a diagram of a configuration of a camera main body according to the third embodiment.
Figure 41:
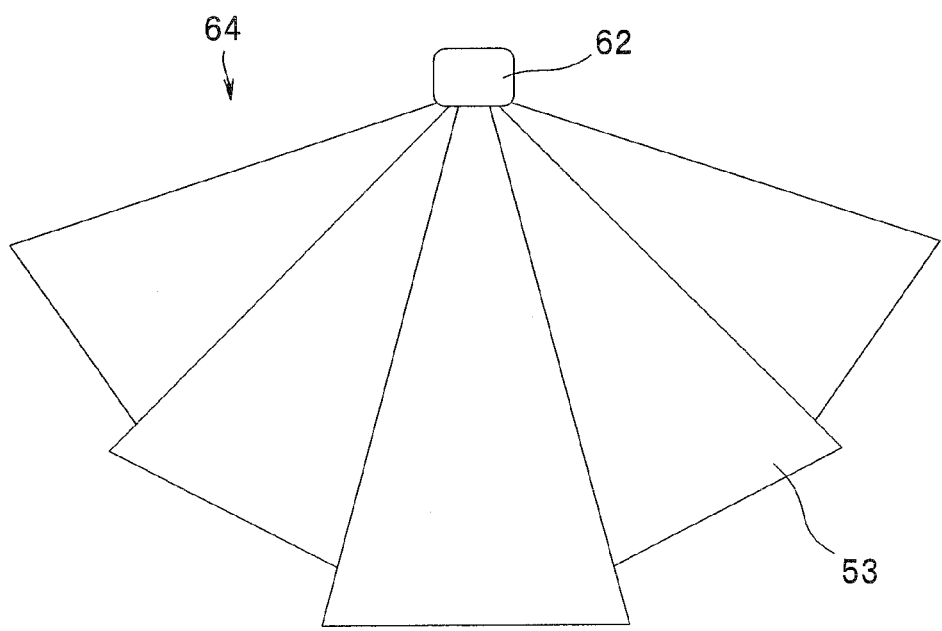
FIG. 41 is a diagram of a configuration of a shield.
Figure 42:
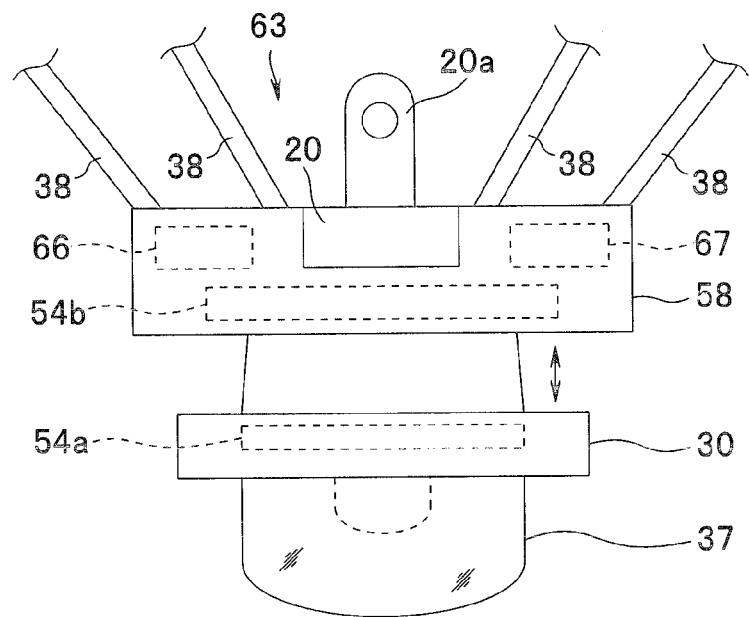
FIG. 42 is a diagram of a configuration of the intra-abdominal cavity set camera in a state in which a shield sheet is removed in the third embodiment.
Figure 43:
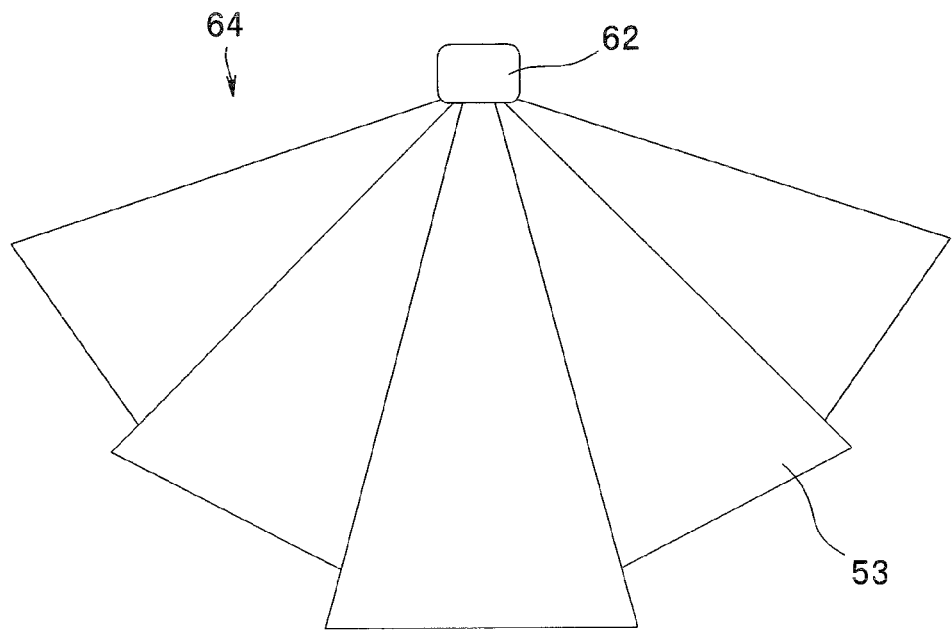
FIG. 43 is a diagram of a state in which the intra-abdominal cavity set camera according to the third embodiment is closed.
Figure 44:
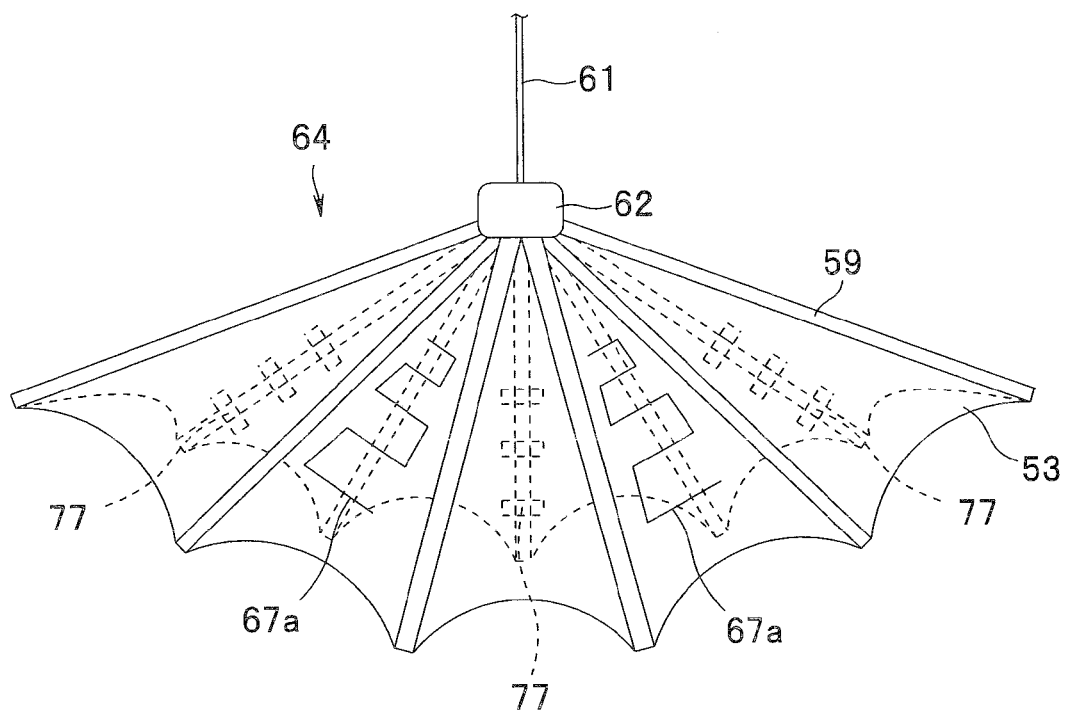
FIG. 44 is a diagram of an intra-abdominal cavity set camera according to a modification of the third embodiment in which illumination units and antennas are provided on the shield sheet.

An endoscope system according to a third embodiment of the present invention is explained below with reference to FIGS. 39 to 44. FIGS. 39 to 44 relate to the third embodiment. FIG. 39 is a diagram of a state in which an intra-abdominal cavity set camera placed in the abdominal cavity is opened. FIG. 40 is a diagram of a configuration of a camera main body. FIG. 41 is a diagram of a configuration of a shield. FIG. 42 is a diagram of a configuration of the intra-abdominal cavity set camera in a state in which a shield sheet is removed. FIG. 43 is a diagram of a state in which the intra-abdominal cavity set camera is closed. FIG. 44 is a diagram of a modification in which illumination units and antennas are provided on the shield sheet.

In the following explanation, components same as those of the endoscope system 1 according to the first and second embodiments are denoted by the same reference numerals and signs. Detailed explanation of the components is omitted.

As shown in FIGS. 39 to 43, the camera 4 according to the present embodiment mainly includes a small camera main body 63, a shield 64, which is covering means as a covering section, having an umbrella structure that is set in an unphotographable state in which the shield 64 is closed and covers the camera main body 63 and a photographable state in which the shield 64 is open, an abdominal wall fixing unit 62, which is holding means as a holding section, that fixes the shield 64 to the abdominal wall 102, and a wire 61 that is connected to the camera main body 63, lifts the camera main body 63, and opens the shield 64.

The camera main body 63 mainly includes an image pickup section 30 having a dome-like transparent cover 37 serving as an observation window and a slide member 58 that slides up and down relative to the image pickup section 30 and serves as a lower lathe of an umbrella to which one ends of receiving ribs 38 of the umbrella are pivotably attached.

The image pickup section 30 shown in FIG. 40 incorporates image pickup units of an image pickup section as image pickup means and illuminating units of an illumination unit as illuminating means, which are not shown in the figure, and includes a magnet 54a. The slide member 58 that slides up and down relative to the image pickup section 30 includes a switch unit 20 that is provided in the center of an upper surface portion and has a wire fastening section 20a to which one end of the wire 61 is connected and fixed, the battery 66, the transmitter 67, and a magnet 54b provided on a lower side.

The switch unit 20 is turned on when the wire fastening section 20a is tugged by the wire 61 and predetermined tension is given thereto and is turned off when the wire fastening section 20a is not tugged by the wire 61. An image pickup function, an illuminating function, and a signal transmitting function of the camera main body 63 are controlled to be turned on and off by the switch unit 20. When the magnets 54a and 54b of the image pickup section 30 and the slide member 58 attract each other, the image pickup section 30 and the slide member 58 adhere to each other in a close state.

The shield 64 shown in FIG. 41 has a shield sheet 53 attached to plural parent ribs 59 (see FIG. 39) of the umbrella and includes the abdominal wall fixing unit 62 that holds one ends of parent ribs 59 to pivot and through which the wire 61 (see FIG. 39) is inserted.

The other ends of the receiving ribs 38, one ends of which are pivotably connected to the image pickup section 30, are pivotably connected to halfway portions of the parent ribs 59. In other words, the camera 4 according to the present embodiment has a shield structure same as an umbrella structure including the plural receiving ribs 38, the plural parent ribs 59, and the shield sheet 53 attached to the parent ribs 59.

When the camera 4 according to the present embodiment configured as explained above is placed in the abdominal cavity 101 in the photographable state by the camera main body 63, the wire 61 is tugged such that the abdominal wall fixing unit 62 comes into contact with and is fixed to the abdominal wall 102. Then, the slide member 58 connected to the wire 61 of the camera main body 63 is tugged upward and separates from the image pickup section 30.

At this point, the receiving ribs 38, one ends of which are pivotably connected to the slide member 58, open to expand the parent ribs 59, one ends of which are pivotably connected to the abdominal wall fixing unit 62. According to the expansion of the parent ribs 59, the shield sheet 53 opens and the camera main body 63 is exposed.

In this way, when the camera 4 is fixed to the abdominal wall 102, as shown in FIG. 39, a state in which the shield 64 open is the photographable state. At this point, the wire fastening section 20a is tugged by the wire 61 and the switch unit 20 applied with predetermined tension is turned on. An image pickup function, an illuminating function, and a signal transmitting function of the camera main body 63 of the camera 4 are turned on.

When the camera 4 is led into the abdominal cavity 101 and collected from the abdominal cavity 101, as shown in FIG. 42 and 43, a state in which the shield 64 is closed is the unphotographable state. In this state, the camera main body 63 is covered with the shield sheet 53. The dome-like transparent cover 37 as the observation window of the camera main body 63 does not touch an organ in the abdominal cavity 101 and soil such as blood is prevented from adhering to the transparent cover 37. Consequently, a field of vision of the camera main body 63 is not blocked and irradiation of illumination light is not prevented by the soil such as blood. Therefore, the camera 4 can perform satisfactory observation of a body tissue.

In the camera 4, when the shield 64 is in the closed state, since the magnets 54a and 54b of the image pickup section 30 and the slide member 58 attract each other, the image pickup section 30 and the slide member 58 adhere to each other and are locked. Therefore, the shield 64 is prevented from unnecessarily opening.

As explained above, with the camera 4 according to the present embodiment, as in the first embodiment, it is possible to prevent an observation window of an observation optical system and illumination windows of an illumination optical system from being soiled when the camera 4 is led into the abdominal cavity 101, so that a field of view during use is not deteriorated and irradiation of illumination light is not disturbed, and acquire a clear observation image.

In the camera 4, in the state in which the shield 64 is closed, the wire fastening section 20a is not tugged by the wire 61. Therefore, the switch unit 20 is turned off and the image pickup function, the illuminating function, and the signal transmitting function of the camera main body 63 of the camera 4 are also turned off. The power supply for the camera 4 is turned on only during photographing of a body organ. Therefore, the lifetime of the battery 66 is extended. Moreover, the incorporated battery 66 only has to be a battery corresponding to power feed adjusted to necessary time of use.

As shown in FIG. 44, the camera 4 may have a configuration in which the antennas 67a are provided in the shield sheet 53 of the shield 64 and the illumination units 77 are provided in the parent ribs 59. Consequently, the directivity of the antennas 67a is improved and the inside of the abdominal cavity 101 can be illuminated in a wide range by the illumination units 77.

It is possible to change an illumination angle and perform concentrated illumination by adjusting an open state (angle) of the shield 64. Further, a mirror film that reflects light may be formed on an inner surface side of the shield sheet 53 to improve an amount of light of illumination.

Fourth Embodiment

Figure 45:
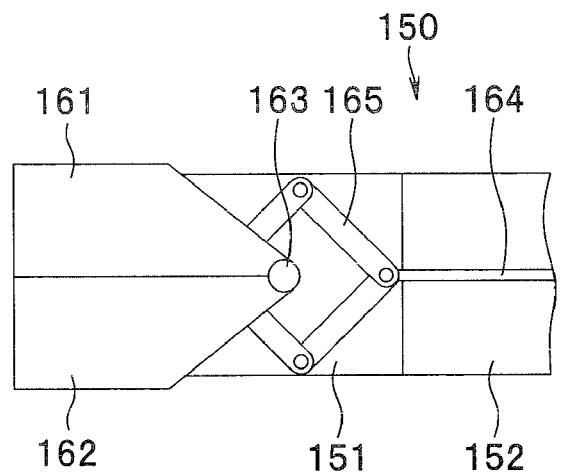
FIG. 45 is a side view of a configuration of an insertion portion of an endoscope in which a cover member covers an observation window and illumination windows provided at a distal end portion in a state in which the observation window and the illumination windows are closed in the third embodiment of the present invention.
Figure 46:
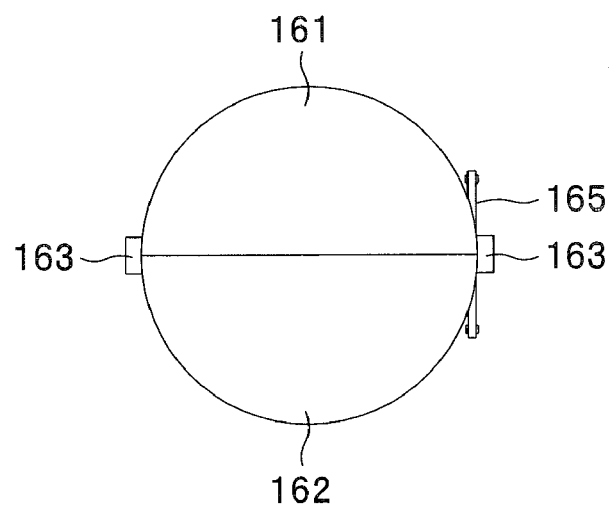
FIG. 46 is a front view of the cover member shown in FIG. 45 in the third embodiment.
Figure 47:
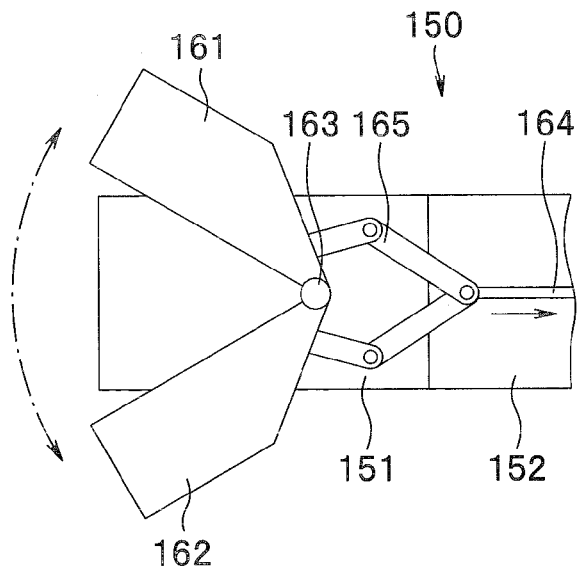
FIG. 47 is a side view of the insertion portion of the endoscope in a state in which the cover member is opened in the third embodiment.
Figure 48:
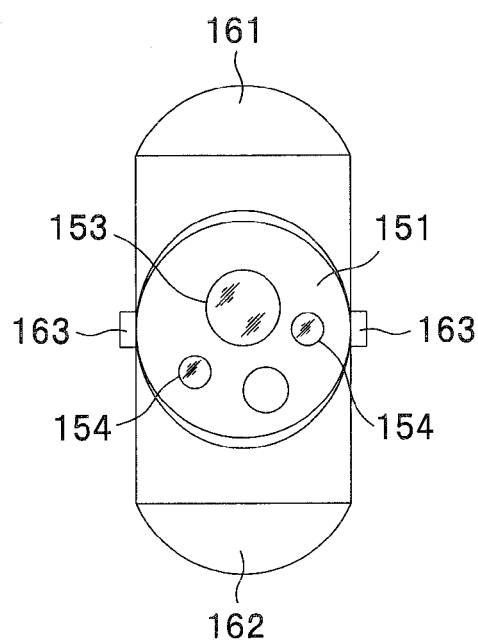
FIG. 48 is a front view of the cover member shown in FIG. 47 in the third embodiment.

An endoscope system according to a fourth embodiment of the present invention is explained below with reference to FIGS. 45 to 48. FIGS. 45 to 48 relate to the fourth embodiment. FIG. 45 is a side view of a configuration of an insertion portion of an endoscope in which a cover member covers an observation window and illumination windows provided at a distal end portion in a state in which the observation window and the illumination windows are closed. FIG. 46 is a front view of the cover member shown in FIG. 45. FIG. 47 is a side view of the insertion portion of the endoscope in a state in which the cover member is opened. FIG. 48 is a front view of the cover member shown in FIG. 47.

In the present embodiment, unlike the intra-abdominal cavity set camera according to the embodiments explained above, an example of covering means serving as a covering section that covers an observation window and illumination windows of an endoscope including a conventionally-used insertion portion is explained.

As shown in FIGS. 45 to 47, an insertion portion 150 of the endoscope includes, at a rigid distal end portion 151, two cover members 161 and 162 that are openably and closably provided and cover a distal end surface. The two cover members 161 and 162 have a shape obtained by dividing a cylinder having a closed distal end portion, which can house the distal end portion 151 of the insertion portion 150, into two. Proximal end portions of the cover members 161 and 162 are coupled by a pivoting shaft 163. When the endoscope is in the unphotographable state, a state in which the cover members 161 and 162 are close to and in contact with each other around the pivoting shaft 163 can be a state in which the distal end portion 151 of the insertion portion 150 is covered. The insertion portion 150 includes a bent section 152 connected to the distal end portion 151.

On the other hand, when the endoscope is in the photographable state, the two cover members 161 and 162 are pivoted in directions away from each other around the pivoting shaft 163. The distal end surface of the distal end portion 151 of the insertion portion 150 can be exposed.

A link mechanism 165 is provided on a proximal end side of the two cover members 161 and 162. The cover members 161 and 162 are pivoted around the pivoting shaft 163 by tugging and relaxation of a wire 164 connected to the link mechanism 165.

As shown in FIGS. 45 and 46, in a state in which the distal end portion 151 is covered with the two cover members 161 and 162, the insertion portion 150 of the endoscope configured as explained above can prevent an observation window 153 of an observation optical system and illumination windows 154 of an illumination optical system from being soiled by a mucous membrane, filth, and the like in a body cavity.

In the insertion portion 150 of the endoscope, as shown in FIGS. 47 and 48, the wire 164 is tugged to open the two cover members 161 and 162 and expose the observation window 153 and the illumination windows 154 provided on the distal end surface of the distal end portion 151. The endoscope can be used in the photographable state.

In this way, in the endoscope including the conventionally-used insertion portion 150 having the configuration different from that of the intra-abdominal cavity set camera according to the embodiments explained above, by providing the two cover members 161 and 162 that open and close, as in the first embodiment, it is possible to prevent the observation window 153 of the observation optical system of the distal end portion (5) and the illumination windows 154 from being soiled when the camera 4 is led into and pulled out from the abdominal cavity, so that a field of view during use is not deteriorated and irradiation of illumination light is not disturbed, and acquire a clear observation image.

The invention according to the embodiments is not limited to the embodiments and the modifications. Besides, at an implementation stage, various modifications can be carried out and obtained without departing from the spirit of the invention. Inventions at various stages are included in the embodiments. Various inventions can be extracted according to appropriate combinations in plural elements disclosed herein.

For example, when the problems to be solved by the invention can be solved and the effects of the invention can be obtained even if several elements are deleted from all the elements described in the embodiments, a configuration in which the elements are deleted can be extracted as an invention.

What is claimed is:

1. A medical apparatus comprising:
    an image pickup section including an observation window, the image pickup section being led into a body;
    a holding section that comes into contact with a body wall inside the body and places and fixes the image pickup section on the body wall;
    a covering section that is connected to the holding section and covers the observation window to set the image pickup section in a non-photographable state;
    a wire that is connected to the covering section via the holding section, and variably controls a covered state of the observation window by the covering section to allow photographing by the image pickup section; and
    a fixing unit engaged with the wire to hold the image pickup section from outside of the body so that the holding section comes into contact with the body wall inside the body.

2. The medical apparatus according to claim 1, wherein the covering section includes at least one of a power supply for driving the image pickup section, a transmitting unit for transmitting image data acquired by the image pickup section to an outside, and an illumination unit that irradiates illumination light on the inside of the body.

3. The medical apparatus according to claim 1, further comprising a switch that turns on and off the image pickup section on the basis of variable control of the covering section for setting the image pickup section in the unphotographable state or the photographable state according to the operation of the wire.

4. The medical apparatus according to claim 2, further comprising a switch that turns on and off the image pickup section on the basis of variable control of the covering section for setting the image pickup section in the unphotographable state or the photographable state according to the operation of the wire.

5. The medical apparatus according to claim 1, wherein the holding section includes: two armor units to be divided that is openably and closably,
    a first armor unit incorporating the image pickup section and, on a first divided surface of which as one surface formed as a plane, disposing the observation window; and
    a second armor unit being connected to the first armor unit to be pivotable around a supporting shaft and having a second divided surface formed as a plane opposed to and in contact with the one surface, and
    the second divided surface coming into contact with the first divided surface to configure the covering section that sets the image pickup section in the unphotographable state.

6. The medical apparatus according to claim 5, wherein the first armor unit and the second armor unit are formed in a semispherical shape to change to a spherical shape in a state in which the first divided surface and the second divided surface are in contact with each other.

7. The medical apparatus according to claim 5, wherein the first armor unit and the second armor unit are formed in a substantial semicolumnar shape, which is obtained by cutting a substantial columnar shape into halves along a longitudinal axis, to change to the substantial columnar shape in a state in which the first divided surface and the second divided surface are in contact with each other.

8. The medical apparatus according to claim 5, wherein
    a dome-like transparent member that covers the observation window is disposed on the first divided surface, and
    a recess for housing the transparent member is provided on the second divided surface.

9. The medical apparatus according to claim 1, further comprising a camera main body that is coupled to the holding section and includes the observation window incorporating the image pickup section, wherein
    the covering section configures plural cover members that are openably and closably disposed in the holding section and cover the camera main body, and
    in a state in which the plural cover members are closed, the camera main body is set in the unphotographable state in which the camera main body is covered together with the observation window.

10. The medical apparatus according to claim 9, wherein
    the plural cover members are opened by operation of the wire and the observation window is exposed to set the image pickup section in the photographable state.

11. The medical apparatus according to claim 9, wherein the plural cover members include, on each of divided surfaces opposed to each other in the closed state, at least one of a transmitting unit for transmitting image data acquired by the image pickup section to an outside and an illumination unit that irradiates illumination light on the inside of the body.

12. The medical apparatus according to claim 1, further comprising a camera main body that is coupled to the wire inserted through the holding section and includes the observation window incorporating the image pickup section, wherein
   the covering section configures a sheet that opens and closes according to tugging and relaxation of the wire and is attached to plural parent ribs to which plural receiving ribs, which are pivotably disposed on the camera main body, are pivotably coupled, and
   in a state in which the sheet is closed, the camera main body is set in the unphotographable state in which the camera main body is covered together with the observation window.

13. The medical apparatus according to claim 12, wherein the plural parent ribs include at least one of a transmitting unit for transmitting image data acquired by the image pickup section to an outside and an illumination unit that irradiates illumination light on the inside of the body.

14. The medical apparatus according to claim 12, further comprising a switch that turns on and off the image pickup section on the basis of variable control of the covering section for setting the image pickup section in the unphotographable state or the photographable state according to the operation of the wire.

* * * * *